(12) United States Patent
Albrecht et al.

(10) Patent No.: US 8,414,487 B2
(45) Date of Patent: Apr. 9, 2013

(54) CIRCULAR SURGICAL RETRACTOR

(75) Inventors: Jeremy J. Albrecht, Rancho Santa Margarita, CA (US); Charles C. Hart, Summerville, SC (US); John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 245 days.

(21) Appl. No.: 13/023,334

(22) Filed: Feb. 8, 2011

(65) Prior Publication Data

US 2011/0130633 A1     Jun. 2, 2011

Related U.S. Application Data

(63) Continuation of application No. 12/768,328, filed on Apr. 27, 2010, now Pat. No. 7,892,172, which is a continuation of application No. 11/548,767, filed on Oct. 12, 2006, now Pat. No. 7,704, 207.

(60) Provisional application No. 60/828,089, filed on Oct. 4, 2006, provisional application No. 60/726,826, filed on Oct. 14, 2005, provisional application No. 60/745,730, filed on Apr. 26, 2006, provisional application No. 60/803,346, filed on May 26, 2006, provisional application No. 60/803,965, filed on Jun. 5, 2006.

(51) Int. Cl.
*A61B 1/32* (2006.01)

(52) U.S. Cl.
USPC ............ 600/208; 600/201; 600/206; 600/233

(58) Field of Classification Search ........... 600/184–246
See application file for complete search history.

(56) References Cited

U.S. PATENT DOCUMENTS

| | | | |
|---|---|---|---|
| 558,364 | A | 4/1896 | Doolittle |
| 1,157,202 | A | 10/1915 | Bates et al. |

(Continued)

FOREIGN PATENT DOCUMENTS

| | | |
|---|---|---|
| DE | 26 05 148 A1 | 8/1977 |
| DE | 33 36 279 C2 | 1/1986 |
| DE | 37 39 532 | 12/1988 |
| DE | 37 37 121 | 5/1989 |
| DE | 296 00 939 | 6/1996 |

(Continued)

OTHER PUBLICATIONS

Harold W. Harrower, M.D. Isolation of Incisions into Body Cavities, The American Journal of Surgery, pp. 824-826.

(Continued)

*Primary Examiner* — Eduardo C Robert
*Assistant Examiner* — Christina Negrellirodriguez
(74) *Attorney, Agent, or Firm* — Cynthia A. Bonner

(57) ABSTRACT

A wound retractor for retracting a surgical incision includes an inner ring, an outer ring and a distensible sleeve coupled to the inner and outer rings. The outer ring includes at least a pair of circular tubes coupled to each other. At least one of the circular tubes includes a lumen and a split that forms open ends. A noncompliant tubular hoop having a split therein is positioned in the lumen. The tubular hoop is oriented with its open ends positioned away from the split of the circular tubes. A core is positioned in the lumen of the tubular hoop. The core has a first end and a second end and is oriented with the ends positioned away from the split in the tubular hoop. The circular tubes may be parallel or may form a helical pattern similar to a Mobius strip.

20 Claims, 29 Drawing Sheets

U.S. PATENT DOCUMENTS

| | | |
|---|---|---|
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds, Jr. et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Banjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |

| | | | | | |
|---|---|---|---|---|---|
| 5,074,878 A | 12/1991 | Bark et al. | 5,364,345 A | 11/1994 | Lowery et al. |
| 5,082,005 A | 1/1992 | Kaldany | 5,364,372 A | 11/1994 | Danks et al. |
| 5,086,763 A | 2/1992 | Hathman | 5,366,446 A | 11/1994 | Tal et al. |
| 5,092,846 A | 3/1992 | Nishijima et al. | 5,366,478 A | 11/1994 | Brinkerhoff et al. |
| 5,104,389 A | 4/1992 | Deem | 5,368,545 A | 11/1994 | Schaller et al. |
| 5,125,396 A | 6/1992 | Ray | 5,375,588 A | 12/1994 | Yoon |
| 5,125,897 A | 6/1992 | Quinn et al. | 5,380,288 A | 1/1995 | Hart et al. |
| 5,127,626 A | 7/1992 | Hilal et al. | 5,383,861 A | 1/1995 | Hempel et al. |
| 5,129,885 A | 7/1992 | Green et al. | 5,385,552 A | 1/1995 | Haber et al. |
| 5,141,498 A | 8/1992 | Christian | 5,385,553 A | 1/1995 | Hart et al. |
| 5,149,327 A | 9/1992 | Oshiyama | 5,385,560 A | 1/1995 | Wulf |
| 5,156,617 A | 10/1992 | Reid | 5,389,080 A | 2/1995 | Yoon |
| 5,158,553 A | 10/1992 | Berry et al. | 5,389,081 A | 2/1995 | Castro |
| 5,159,921 A | 11/1992 | Hoover | 5,391,153 A | 2/1995 | Haber et al. |
| 5,161,773 A | 11/1992 | Tower | 5,391,156 A | 2/1995 | Hildwein et al. |
| 5,167,636 A | 12/1992 | Clement | 5,395,367 A | 3/1995 | Wilk |
| 5,167,637 A | 12/1992 | Okada et al. | 5,403,264 A | 4/1995 | Wohlers et al. |
| 5,176,648 A | 1/1993 | Holmes et al. | 5,403,336 A | 4/1995 | Kieturakis et al. |
| 5,176,662 A | 1/1993 | Bartholomew et al. | 5,407,433 A | 4/1995 | Loomas |
| 5,176,697 A | 1/1993 | Hasson et al. | 5,411,483 A | 5/1995 | Loomas |
| 5,178,162 A | 1/1993 | Bose | 5,413,571 A | 5/1995 | Katsaros et al. |
| 5,180,365 A | 1/1993 | Ensminger et al. | 5,423,848 A | 6/1995 | Washizuka et al. |
| 5,183,471 A | 2/1993 | Wilk | 5,429,609 A | 7/1995 | Yoon |
| 5,188,595 A | 2/1993 | Jacobi | 5,431,676 A | 7/1995 | Durdal et al. |
| 5,188,607 A | 2/1993 | Wu | 5,437,683 A | 8/1995 | Neumann et al. |
| 5,192,301 A | 3/1993 | Kamiya et al. | 5,439,455 A | 8/1995 | Kieturakis et al. |
| 5,197,955 A | 3/1993 | Stephens et al. | 5,441,486 A | 8/1995 | Yoon |
| 5,207,656 A | 5/1993 | Kranys | 5,443,452 A | 8/1995 | Hart et al. |
| 5,209,737 A | 5/1993 | Rirchart et al. | 5,456,284 A | 10/1995 | Ryan et al. |
| 5,211,370 A | 5/1993 | Powers | 5,460,170 A | 10/1995 | Hammerslag |
| 5,211,633 A | 5/1993 | Stouder, Jr. | 5,460,616 A | 10/1995 | Weinstein et al. |
| 5,213,114 A | 5/1993 | Bailey, Jr. | 5,468,248 A | 11/1995 | Chin et al. |
| 5,226,890 A | 7/1993 | Ianniruberto et al. | 5,476,475 A | 12/1995 | Gadberry |
| 5,234,455 A | 8/1993 | Mulhollan | 5,480,410 A | 1/1996 | Cuschieri et al. |
| 5,241,968 A | 9/1993 | Slater | 5,486,426 A | 1/1996 | McGee et al. |
| 5,242,400 A | 9/1993 | Blake, III et al. | 5,490,843 A | 2/1996 | Hildwein et al. |
| 5,242,409 A | 9/1993 | Buelna | 5,492,304 A | 2/1996 | Smith et al. |
| 5,242,412 A | 9/1993 | Blake, III | 5,496,280 A | 3/1996 | Vandenbroek et al. |
| 5,242,415 A | 9/1993 | Kantrowitz et al. | 5,503,112 A | 4/1996 | Luhman et al. |
| 5,248,304 A | 9/1993 | Vigdorchik et al. | 5,507,758 A | 4/1996 | Thomason et al. |
| 5,256,150 A | 10/1993 | Quiachon et al. | 5,508,334 A | 4/1996 | Chen |
| 5,257,973 A | 11/1993 | Villasuso | 5,511,564 A | 4/1996 | Wilk |
| 5,257,975 A | 11/1993 | Foshee | 5,514,109 A | 5/1996 | Mollenauer et al. |
| 5,259,366 A | 11/1993 | Reydel et al. | 5,514,133 A | 5/1996 | Golub et al. |
| 5,261,883 A | 11/1993 | Hood et al. | 5,514,153 A | 5/1996 | Bonutti |
| 5,262,468 A | 11/1993 | Chen | 5,518,278 A | 5/1996 | Sampson |
| 5,263,922 A | 11/1993 | Sova et al. | 5,520,632 A | 5/1996 | Leveen |
| 5,269,763 A | 12/1993 | Boehmer et al. | 5,522,791 A | 6/1996 | Leyva |
| 5,269,772 A | 12/1993 | Wilk | 5,522,824 A | 6/1996 | Ashby |
| 5,273,449 A | 12/1993 | Mattis et al. | 5,524,644 A | 6/1996 | Crook |
| 5,273,545 A | 12/1993 | Hunt et al. | 5,526,536 A | 6/1996 | Cartmill |
| D343,236 S | 1/1994 | Quigley et al. | 5,531,758 A | 7/1996 | Uschold et al. |
| 5,279,575 A | 1/1994 | Sugarbaker | 5,538,509 A | 7/1996 | Dunlap et al. |
| 5,290,310 A | 3/1994 | Makower et al. | 5,540,648 A | 7/1996 | Yoon |
| D346,022 S | 4/1994 | Quigley et al. | 5,540,711 A | 7/1996 | Kieturakis et al. |
| 5,299,582 A | 4/1994 | Potts | 5,545,150 A | 8/1996 | Danks et al. |
| 5,300,034 A | 4/1994 | Behnke | 5,545,179 A | 8/1996 | Williamson, IV |
| 5,300,035 A | 4/1994 | Clement | 5,549,563 A | 8/1996 | Kronner |
| 5,300,036 A | 4/1994 | Mueller et al. | 5,549,637 A | 8/1996 | Crainich |
| 5,308,336 A | 5/1994 | Hart et al. | 5,554,124 A | 9/1996 | Alvarado |
| 5,309,896 A | 5/1994 | Moll et al. | 5,562,632 A | 10/1996 | Davila et al. |
| 5,312,391 A | 5/1994 | Wilk | 5,562,677 A | 10/1996 | Hildwein et al. |
| 5,314,417 A | 5/1994 | Stephens et al. | 5,562,688 A | 10/1996 | Riza |
| 5,316,541 A | 5/1994 | Fischer | 5,571,115 A | 11/1996 | Nicholas |
| 5,320,611 A | 6/1994 | Bonutti et al. | 5,571,137 A | 11/1996 | Marlow et al. |
| 5,330,437 A | 7/1994 | Durman | 5,575,799 A | 11/1996 | Bolanos et al. |
| 5,330,486 A | 7/1994 | Wilk | 5,577,993 A | 11/1996 | Zhu et al. |
| 5,330,497 A | 7/1994 | Freitas et al. | 5,578,048 A | 11/1996 | Pasqualucci et al. |
| 5,331,975 A | 7/1994 | Bonutti | 5,580,344 A | 12/1996 | Hasson |
| 5,334,143 A | 8/1994 | Carroll | 5,584,850 A | 12/1996 | Hart et al. |
| 5,336,192 A | 8/1994 | Palestrant | 5,601,579 A | 2/1997 | Semertzides |
| 5,336,708 A | 8/1994 | Chen | 5,601,581 A | 2/1997 | Fogarty et al. |
| 5,338,313 A | 8/1994 | Mollenauer et al. | 5,603,702 A | 2/1997 | Smith et al. |
| 5,342,315 A | 8/1994 | Rowe et al. | 5,607,443 A | 3/1997 | Kieturakis et al. |
| 5,342,385 A | 8/1994 | Norelli et al. | 5,620,415 A | 4/1997 | Lucey et al. |
| 5,350,364 A | 9/1994 | Stephens et al. | 5,620,420 A | 4/1997 | Kriesel |
| 5,353,786 A | 10/1994 | Wilk | 5,628,732 A | 5/1997 | Antoon, Jr. et al. |
| 5,354,280 A | 10/1994 | Haber et al. | 5,632,284 A | 5/1997 | Graether |
| 5,360,417 A | 11/1994 | Gravener et al. | 5,632,979 A | 5/1997 | Goldberg et al. |

| | | | | | |
|---|---|---|---|---|---|
| 5,634,911 A | 6/1997 | Hermann et al. | 5,906,577 A | 5/1999 | Beane et al. |
| 5,634,936 A | 6/1997 | Linden et al. | 5,913,847 A | 6/1999 | Yoon |
| 5,634,937 A | 6/1997 | Mollenauer et al. | 5,916,198 A | 6/1999 | Dillow |
| 5,636,645 A | 6/1997 | Ou | 5,916,232 A | 6/1999 | Hart |
| 5,640,977 A | 6/1997 | Leahy et al. | 5,919,476 A | 7/1999 | Fischer et al. |
| 5,643,301 A | 7/1997 | Mollenauer | 5,931,832 A | 8/1999 | Jensen |
| 5,649,550 A | 7/1997 | Crook | 5,947,922 A | 9/1999 | MacLeod |
| 5,651,771 A | 7/1997 | Tangherlini et al. | 5,951,467 A | 9/1999 | Picha et al. |
| 5,653,705 A | 8/1997 | de la Torre et al. | 5,951,588 A | 9/1999 | Moenning |
| 5,657,963 A | 8/1997 | Hinchliffe et al. | 5,957,888 A | 9/1999 | Hinchiffe et al. |
| 5,658,272 A | 8/1997 | Hasson | 5,957,913 A | 9/1999 | de la Torre et al. |
| 5,658,306 A | 8/1997 | Kieturakis et al. | 5,962,572 A | 10/1999 | Chen |
| 5,662,615 A | 9/1997 | Blake, III | 5,964,781 A | 10/1999 | Mollenauer et al. |
| 5,672,168 A | 9/1997 | de la Torre et al. | 5,976,174 A | 11/1999 | Ruiz |
| 5,681,341 A | 10/1997 | Lunsford et al. | 5,989,232 A | 11/1999 | Yoon |
| 5,683,378 A | 11/1997 | Christy | 5,989,233 A | 11/1999 | Yoon |
| 5,685,854 A | 11/1997 | Green et al. | 5,989,266 A | 11/1999 | Foster |
| 5,685,857 A | 11/1997 | Negus et al. | 5,993,471 A | 11/1999 | Riza et al. |
| 5,697,914 A | 12/1997 | Brimhall | 5,993,485 A | 11/1999 | Beckers |
| 5,707,703 A | 1/1998 | Rothrum et al. | 5,994,450 A | 11/1999 | Pearce |
| 5,709,664 A | 1/1998 | Vandenbroek et al. | 5,997,515 A | 12/1999 | de la Torre et al. |
| 5,713,858 A | 2/1998 | Heruth et al. | 6,004,303 A | 12/1999 | Peterson |
| 5,713,869 A | 2/1998 | Morejon | 6,010,494 A | 1/2000 | Schafer et al. |
| 5,720,730 A | 2/1998 | Blake, III | 6,017,355 A | 1/2000 | Hessel et al. |
| 5,725,536 A | 3/1998 | Oberlin et al. | 6,018,094 A | 1/2000 | Fox |
| 5,728,103 A | 3/1998 | Picha et al. | 6,024,736 A | 2/2000 | de la Torre et al. |
| 5,730,748 A | 3/1998 | Fogarty et al. | 6,025,067 A | 2/2000 | Fay |
| 5,735,791 A | 4/1998 | Alexander et al. | 6,033,426 A | 3/2000 | Kaji |
| 5,738,628 A | 4/1998 | Sierocuk et al. | 6,033,428 A | 3/2000 | Sardella |
| 5,741,234 A | 4/1998 | Aboul-Hosn | 6,035,559 A | 3/2000 | Freed et al. |
| 5,741,298 A | 4/1998 | MacLeod | 6,042,573 A | 3/2000 | Lucey |
| 5,743,884 A | 4/1998 | Hasson et al. | 6,045,535 A | 4/2000 | Ben Nun |
| 5,749,882 A | 5/1998 | Hart et al. | 6,048,309 A | 4/2000 | Flom et al. |
| 5,753,150 A | 5/1998 | Martin et al. | 6,050,871 A | 4/2000 | Chen |
| 5,755,660 A | 5/1998 | Tyagi | 6,053,934 A | 4/2000 | Andrews et al. |
| 5,760,117 A | 6/1998 | Chen | 6,059,816 A | 5/2000 | Moenning |
| 5,769,783 A | 6/1998 | Fowler | 6,066,117 A | 5/2000 | Fox et al. |
| 5,782,812 A | 7/1998 | Hart et al. | 6,068,639 A | 5/2000 | Fogarty et al. |
| 5,782,817 A | 7/1998 | Franzel et al. | 6,077,288 A | 6/2000 | Shimomura |
| 5,782,859 A | 7/1998 | Nicholas et al. | 6,086,603 A | 7/2000 | Termin et al. |
| 5,788,676 A | 8/1998 | Yoon | 6,090,043 A | 7/2000 | Austin et al. |
| 5,792,119 A | 8/1998 | Marx | 6,099,506 A | 8/2000 | Macoviak et al. |
| 5,795,290 A | 8/1998 | Bridges | 6,110,154 A | 8/2000 | Shimomura et al. |
| 5,803,919 A | 9/1998 | Hart et al. | 6,123,689 A | 9/2000 | To |
| 5,803,921 A | 9/1998 | Bonadio | 6,142,935 A | 11/2000 | Flom et al. |
| 5,803,923 A | 9/1998 | Singh-Derewa et al. | 6,142,936 A | 11/2000 | Beane et al. |
| 5,807,350 A | 9/1998 | Diaz | 6,149,642 A | 11/2000 | Gerhart et al. |
| 5,810,712 A | 9/1998 | Dunn | 6,150,608 A | 11/2000 | Wambeke et al. |
| 5,810,721 A | 9/1998 | Mueller et al. | 6,159,182 A | 12/2000 | Davis |
| 5,813,409 A | 9/1998 | Leahy et al. | 6,162,172 A | 12/2000 | Cosgrove et al. |
| 5,814,026 A | 9/1998 | Yoon | 6,162,196 A | 12/2000 | Hart et al. |
| 5,817,062 A | 10/1998 | Flom et al. | 6,162,206 A | 12/2000 | Bindokas |
| 5,819,375 A | 10/1998 | Kastner | 6,163,949 A | 12/2000 | Neuenschwander |
| 5,820,555 A | 10/1998 | Watkins, III et al. | 6,164,279 A | 12/2000 | Tweedle |
| 5,820,600 A | 10/1998 | Carlson et al. | 6,171,282 B1 | 1/2001 | Ragsdale |
| 5,830,191 A | 11/1998 | Hildwein et al. | 6,183,486 B1 | 2/2001 | Snow et al. |
| 5,832,925 A | 11/1998 | Rothrum | 6,197,002 B1 | 3/2001 | Peterson |
| 5,836,871 A | 11/1998 | Wallace et al. | 6,217,555 B1 | 4/2001 | Hart et al. |
| 5,841,298 A | 11/1998 | Huang | 6,217,590 B1 | 4/2001 | Levinson |
| 5,842,971 A | 12/1998 | Yoon | 6,224,612 B1 | 5/2001 | Bates et al. |
| 5,848,992 A | 12/1998 | Hart et al. | 6,228,063 B1 | 5/2001 | Aboul-Hosn |
| 5,853,395 A | 12/1998 | Crook et al. | 6,238,373 B1 | 5/2001 | de la Torre et al. |
| 5,853,417 A | 12/1998 | Fogarty et al. | 6,241,768 B1 | 6/2001 | Agarwal et al. |
| 5,857,461 A | 1/1999 | Levitsky et al. | 6,254,533 B1 | 7/2001 | Fadem et al. |
| 5,860,995 A | 1/1999 | Berkelaar | 6,254,534 B1 | 7/2001 | Butler et al. |
| 5,865,728 A | 2/1999 | Moll et al. | 6,258,065 B1 | 7/2001 | Dennis et al. |
| 5,865,729 A | 2/1999 | Meehan et al. | 6,264,604 B1 | 7/2001 | Kieturakis et al. |
| 5,865,807 A | 2/1999 | Blake, III | 6,267,751 B1 | 7/2001 | Mangosong |
| 5,865,817 A | 2/1999 | Moenning et al. | 6,276,661 B1 | 8/2001 | Laird |
| 5,871,474 A | 2/1999 | Hermann et al. | 6,287,280 B1 | 9/2001 | Lampropoulos et al. |
| 5,876,413 A | 3/1999 | Fogarty et al. | 6,315,770 B1 | 11/2001 | de la Torre et al. |
| 5,879,368 A | 3/1999 | Hoskin et al. | 6,319,246 B1 | 11/2001 | de la Torre et al. |
| 5,882,344 A | 3/1999 | Stouder, Jr. | 6,322,541 B2 | 11/2001 | West |
| 5,884,639 A | 3/1999 | Chen | 6,325,384 B1 | 12/2001 | Berry, Sr. et al. |
| 5,894,843 A | 4/1999 | Benetti et al. | 6,346,074 B1 | 2/2002 | Roth |
| 5,895,377 A | 4/1999 | Smith et al. | 6,371,968 B1 | 4/2002 | Kogasaka et al. |
| 5,899,208 A | 5/1999 | Bonadio | 6,382,211 B1 | 5/2002 | Crook |
| 5,899,913 A | 5/1999 | Fogarty et al. | 6,383,162 B1 | 5/2002 | Sugarbaker |
| 5,904,703 A | 5/1999 | Gilson | 6,391,043 B1 | 5/2002 | Moll et al. |

| | | |
|---|---|---|
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Liu et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,850,667 B2 | 12/2010 | Gresham |
| 7,867,164 B2 | 1/2011 | Butler et al. |

| | | |
|---|---|---|
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,896,889 B2 | 3/2011 | Mazzocchi et al. |
| 7,909,760 B2 | 3/2011 | Albrecht et al. |
| 7,913,697 B2 | 3/2011 | Nguyen et al. |
| 7,930,782 B2 | 4/2011 | Chen |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlbert et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkler, II et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0156023 A1 | 7/2007 | Frasier et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270654 A1 | 11/2007 | Pignato et al. |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0103366 A1 | 5/2008 | Banchieri et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegal et al. |

| | | | |
|---|---|---|---|
| 2010/0249524 A1 | 9/2010 | Ransden et al. | |
| 2010/0249525 A1 | 9/2010 | Shelton, IV et al. | |
| 2010/0249694 A1 | 9/2010 | Choi et al. | |
| 2010/0261972 A1 | 10/2010 | Widenhouse et al. | |
| 2010/0261975 A1 | 10/2010 | Huey et al. | |
| 2010/0286484 A1 | 11/2010 | Stellon et al. | |
| 2010/0298646 A1 | 11/2010 | Stellon et al. | |
| 2010/0305407 A1 | 12/2010 | Farley | |
| 2011/0021877 A1 | 1/2011 | Fortier et al. | |
| 2011/0028891 A1 | 2/2011 | Okoniewski | |
| 2011/0034935 A1 | 2/2011 | Kleyman | |
| 2011/0034946 A1 | 2/2011 | Kleyman | |
| 2011/0034947 A1 | 2/2011 | Kleyman | |
| 2011/0071462 A1 | 3/2011 | Ewers et al. | |
| 2011/0071463 A1 | 3/2011 | Ewers et al. | |

FOREIGN PATENT DOCUMENTS

| | | |
|---|---|---|
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1 407 715 | 4/2004 |
| EP | 1 609 429 | 12/2005 |
| EP | 2044889 | 4/2009 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO95/07056 | 3/1995 |
| WO | WO 95/07056 | 3/1995 |
| WO | WO95/22289 | 8/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO00/32116 | 6/2000 |
| WO | WO 00/32116 | 6/2000 |
| WO | WO 00/32119 | 6/2000 |
| WO | WO 00/32120 | 6/2000 |
| WO | WO 00/35356 | 6/2000 |
| WO | WO00/54675 | 9/2000 |
| WO | WO 00/54675 | 9/2000 |
| WO | WO00/54676 | 9/2000 |
| WO | WO 00/54676 | 9/2000 |
| WO | WO 00/54677 | 9/2000 |
| WO | WO00/54677 | 9/2000 |
| WO | WO 01/08563 | 2/2001 |
| WO | WO01/08581 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO02/34108 | 5/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO03/032819 | 4/2003 |
| WO | WO 03/032819 | 4/2003 |
| WO | WO03/034908 | 5/2003 |
| WO | WO 03/034908 | 5/2003 |
| WO | WO03/061480 | 7/2003 |
| WO | WO 03/061480 | 7/2003 |
| WO | WO 03/077726 | 9/2003 |
| WO | WO 03/077726 A2 | 9/2003 |
| WO | WO 03/103548 | 12/2003 |
| WO | WO 03/103548 A1 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/057982 | 6/2006 |
| WO | WO 2006/059318 | 6/2006 |
| WO | WO 2006/100658 | 9/2006 |
| WO | WO 2007/044849 | 4/2007 |
| WO | WO 2008/011358 | 1/2008 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

European Patent Office, European Search Report for European Patent No. 11172709.5, dated Aug. 16, 2011.

European Patent Office, European Search Report for European Patent No. 11172706.1, dated Aug. 16, 2011.
5,334,646, Aug. 1994, Chen.
U.S. Appl. No. 10/902,756, filed Jul. 29, 2004, Title: Hand Access Port Device, now abandoned.
U.S. Appl. No. 10/802,125, filed Mar. 15, 2004, Title: Surgical Guide Valve, now abandoned.
U.S. Appl. No. 10/927,551, filed Aug. 25, 2004, Title: Surgical Access System, now abandoned.
U.S. Appl. No. 10/695,295, filed Oct. 28, 2003, Title: Surgical Gel Seal.
U.S. Appl. No. 11/132,741, filed May 18, 2005, Title: Gas-Tight Seal Accomodating Surgical Instruments With a Wide Range of Diameters.
U.S. Appl. No. 11/245,709, filed Oct. 7, 2005, Title: Surgical Access System.
U.S. Appl. No. 11/330,661, filed Jan. 12, 2006, Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and The Written Opinion of the International Searching Authority for International Application No. PCT/US2006/040154, mailed Jan. 30, 2007.
European Patent Office, International Search Report and The Written Opinion of the International Searching Authority for International Application No. PCT/US2006/040073, mailed Jan. 26, 2007.
European Patent Office, International Search Report and The Written Opinion of the International Searching Authority for International Application No. PCT/US2006/039905, mailed Jan. 17, 2007.
European Patent Office, International Search Report and The Written Opinion of the International Searching Authority for International Application No. PCT/US2006/039883, mailed Jan. 31, 2007.
European Patent Office, International Search Report and The Written Opinion of the International Searching Authority for International Application No. PCT/US2006/039800, mailed Apr. 16, 2007.
European Patent Office, International Search Report and The Written Opinion of the International Searching Authority for International Application No. PCT/US2006/039799, mailed Mar. 27, 2007.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484.
International Searching Authority/US, International Search Report and the Written Opinion of the International Searching Authority for International Application No. PCT/US01/29682.
McSweeney, Cannulation of the Rumen in Cattle and Buffaloes, Australian Veterinary Journal, Aug. 1989, vol. 66, No. 8, pp. 266-268.

Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.

Office Action in co-pending U.S. Appl. No. 12/360,634, dated Jan. 24, 2011 in 12 pages.

Office Action in co-pending U.S. Appl. No. 12/360,710, dated Jan. 24, 2011 in 12 pages.

Technical Note: Development of Duodenal Cannula for Sheep, Faculty of Agriculture and School of Medicine Tohokju University, Sendai 981, Japan.

The International Bureau of WIPO, International Preliminary Report on Patentability, dated Aug. 29, 2006, for International Application No. PCT/US2004/028250.

The International Bureau of WIPO, International Preliminary Report on Patentability, dated Apr. 16, 2008, for International Application No. PCT/US2006/039799.

The International Bureau of WIPO, International Preliminary Report on Patentability for International Application No. PCT/US2006/039800 dated Apr. 16, 2008.

Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.

Kagaya, Laparascopic cholecystecomy via two ports, using the "Twin-Port" system, J. Hepatobiliary Pancreat Surg (2001) 8:76-80.

International Search Report and Written Opinion in PCT/IE2005/000113 mailed on Feb. 22, 2006.

International Search Report and Written Opinion in PCT/IE2007/000050 mailed on Aug. 13, 2007.

Declaration of John R. Brustad dated Dec. 10, 2009, submitted in U.S. Appl. No. 11/548,955, including Appendices A-D regarding product sales brochures and production drawings from 2001 and 2005.

The International Searching Authority, The International Search Report and Written Opinion of the International Searching Authority for International Application No. PCT/US08/63445, mailed Sep. 29, 2008.

The International Searching Authority, The International Search Report and Written Opinion of the International Searching Authority for International Application No. PCT/US08/063463 mailed Sep. 10, 2008.

The International Bureau of WIPO, International Preliminary Report on Patentability for International Application No. PCT/US2008/063463, dated Nov. 17, 2009, entitled "Surgical Retractor".

The International Bureau of WIPO, International Preliminary Report on Patentability for International Application No. PCT/US08/63445, issued Nov. 17, 2009, entitled "Surgical Retractor with Gel Pad".

International Searching Authority—US, International Search Report and Written Opinion of the International Searching Authority for International Application No. PCT/US04/25511, mailed Nov. 7, 2007.

International Bureau of WIPO, International Report on Patentability for International Application No. PCT/US04/25511, mailed Dec. 6, 2007.

European Patent Office, International Search Report and Written Opinion for International Application No. PCT/US2012/037111, titled Wound Retractor, mailed Aug. 30, 2012.

European Patent Office, Supplementary European Search Report for European Patent Application No. 08755322, dated Apr. 18, 2012.

European Patent Office, Supplementary European Search Report for European Patent Application No. 08755336, dated Jun. 15, 2012.

5,344,646, withdrrawn, Chen (withdrawn).

Horigane, et al., Technical Note: Development of a Duodoenal Cannula for Sheep, Journal of Animal Science, Apr. 1992, vol. 70, Issue 4, pp. 1216-1219.

Horigane, et al., Silicone Rumen Cannula with a Soft Cylindrical Part and a Hard Flange, Journal of Dairy Science, Nov. 1989, vol. 72, No. 11, pp. 3230-3232.

McSweeney, Cannullation of the Rumen in Cattle and Buffaloes, Australian Veterinary Journal, Aug. 1989, vol. 66, No. 8, pp. 266-268.

Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.

European Patent Office, International Search Report and Written Opinion of the International Searching Authority for International Application No. PCT/US2006/039883, mailed Jan. 31, 2007.

Co-Pending U.S. Appl. No. 11/548,781, filed Oct. 12, 2006; Title: Wound Retractor With Gel Cap.

Co-Pending U.S. Appl. No. 11/548,955, filed Oct. 12, 2006; Title: Hand Access Laparoscopic Device.

Co-Pending U.S. Appl. No. 11/564,409, filed Nov. 29, 2006; Title: Surgical Instrument Access Device.

Co-Pending U.S. Appl. No. 10/381,220, filed Mar. 20, 2003; Title: Surgical Access Apparatus and Method.

Co-Pending U.S. Appl. No. 10/516,198, filed Nov. 30, 2004; Title: Wound Retractor.

Co-Pending U.S. Appl. No. 10/927,551, filed Aug. 25, 2004; Title: Surgical Access System.

Co-Pending U.S. Appl. No. 11/244,647, filed Oct. 5, 2005; Title: Surgical Access Apparatus and Method.

Co-Pending U.S. Appl. No. 11/245,709, filed Oct. 7, 2005; Title: Surgical Access System.

Co-Pending U.S. Appl. No. 11/330,661, filed Jan. 12, 2006; Title: Sealed Surgical Access Device.

Co-Pending U.S. Appl. No. 11/548,746, filed Oct. 12, 2006; Title: Method of Making a Hand Access Laparoscopic Device.

Co-Pending U.S. Appl. No. 11/548,758, filed Oct. 12, 2006; Title: Split Hoop Wound Retractor With Gel Pad.

Co-Pending U.S. Appl. No. 11/548,765, filed Oct. 12, 2006; Title: Split Hoop Wound Retractor.

Co-Pending U.S. Appl. No. 11/755,305, filed May 30, 2007; Title: Wound Retraction Apparatus and Method.

Co-Pending U.S. Appl. No. 12/108,400, filed Apr. 23, 2008; Title: Wound Retraction Apparatus and Method.

European Patent Office, International Search Report and the Writiten Opinion of the International Searching Authority for PCT Application No. PCT/US2006/039799 mailed Mar. 27, 2007.

European Patent Office, International Search Report and the Writiten Opinion of the International Searching Authority for PCT Application No. PCT/US2004/05484.

European Patent Office, International Search Report and the Writiten Opinion of the International Searching Authority for PCT Application No. PCT/US2006/039800 mailed Apr. 16, 2007.

European Patent Office, International Search Report and the Writiten Opinion of the International Searching Authority for PCT Application No. PCT/US2006/039905, mailed Jan. 17, 2007.

European Patent Office, International Search Report and the Writiten Opinion of the International Searching Authority for PCT Application No. PCT/US2006/040073, Jan. 26, 2007.

European Patent Office, International Search Report and the Writiten Opinion of the International Searching Authority for PCT Application No. PCT/US2006/040154, mailed Jan. 30, 2007.

European Patent Office, Supplementary European Search Report for European Application No. EP 01 97 3379, dated Jul. 5, 2007, based on International Patent Application No. PCT/US01/29682, filed Sep. 21, 2001.

International Search Report and Written Opinion of the International Searching Authority for PCT application No. PCT/US01/129682.

The International Bureau of WIPO, The International Preliminary Report on Patentability for International Application No. PCT/US2006/039883, mailed Apr. 24, 2008.

The International Bureau of WIPO, International Preliminary Report on Patentability dated Apr. 16, 2008 for PCT Application No. PCT/US2006/039799.

The International Bureau of WIPO, International Preliminary Report on Patentability dated Apr. 16, 20088 for PCT Application No. PCT/US2006/039800.

Declaration of John R. Brustad Under 37 C.F. R. 1.132, dated Dec. 10, 2009.

"Applied GelPort™ Advanced Access Device" product sales brochure dated 2001.

"Cap Ring" production drawing dated Jan. 19, 2001.

"Gelport® Laparoscopic Hand Access System" product sales brochure dated 2005.

"Cap Ring Medium" production drawing dated Aug. 16, 2005.

CIRCULAR SURGICAL RETRACTOR

CROSS-REFERENCE TO RELATED APPLICATIONS

This application is a continuation of U.S. application Ser. No. 12/768,328, filed Apr. 27, 2010, now U.S. Pat. No. 7,892,172, which is a continuation of U.S. application Ser. No. 11/548,767, filed Oct. 12, 2006, now U.S. Pat. No. 7,704,207, which claims the benefit of: U.S. Application No. 60/828,089, filed Oct. 4, 2006; U.S. Application No. 60/803,965, filed Jun. 5, 2006; U.S. Application No. 60/803,346, filed May 26, 2006; U.S. Application No. 60/745,730, filed Apr. 26, 2006; and U.S. Application No. 60/726,826, filed Oct. 14, 2005, the entire disclosures of which are incorporated by reference.

BACKGROUND

This invention relates generally to surgical wound retractors and more specifically to circular wound retractors that provide circumferential retraction of an incision or wound and also provide isolation of the surgical incision or wound from the lumen of the retractor.

Retraction and isolation of a surgical incision can be an important element associated with a surgical procedure. Adequate access may be provided by a circumferential retraction device so that a surgeon may operate in a clear and open, generally unrestricted field. In addition, a circumferential retractor having a fluid impermeable sleeve extending through the incision or wound may prevent excessive bleeding or contamination of adjacent tissue. In some surgeries, it is important to avoid contaminating the incision or wound site.

Common procedures for placing current circumferential wound retraction devices involve placement of an internal retention ring that is coupled to a thin-walled sleeve or tube that is further coupled to an external retention member. The external retention member is wound or turned upon itself to wind the sleeve upon the external retention member. The physics associated with winding a sleeve upon a circular winding collar or external retention member dictate that ample energy must be applied to the external winding motion to provide adequate circumferential retraction of a linear incision. The initial windings of the process are not overwhelming, however, as the process continues the retraction becomes more difficult and the mechanical advantages first appreciated begin to dissipate. The final windings are more difficult since a balance between the force required to wind the sleeve upon the external retention member must be balanced with the force acting to unwind the sleeve from the external retention member.

There remains a need to provide a substantially rigid, noncompliant circumferential retractor that easily shortens the length of an associated tubular sleeve coupled to an internal retention member so that the shortening of the sleeve results in dramatic retraction of an incision or wound. Additionally, the retention members must remain substantially circular so that the incision is retracted symmetrically.

SUMMARY

The invention is directed to an adjustable wound retractor adapted to retract a surgical incision in a body wall to a desired diameter. The wound retractor includes a first, inner ring, a second, outer ring and a distensible sleeve coupled to the first, inner ring and to the second, outer ring. The first, inner ring is adapted to be inserted into the incision and to be juxtaposed with an inner surface of the body wall. The second, outer ring is adapted for juxtaposition with an outer surface of the body wall. The outer ring includes a first substantially circular tube having a first lumen. The first circular tube is made of a flexible material. The outer ring also includes a second substantially circular tube that is spaced axially from the first circular tube and is coupled to the first circular tube of the outer ring. The second circular tube has a second lumen. The second circular tube is made of a flexible material. The outer ring also includes a first rigid, noncompliant tubular hoop having a split therein. The split forms open ends of the first tubular hoop. The first tubular hoop is positioned in the first lumen of the first circular tube of the outer ring. The outer ring also includes a second rigid, noncompliant tubular hoop having a split therein with the split forming open ends of the second tubular hoop. The second tubular hoop is positioned in the second lumen of the second circular tube of the outer ring. The outer ring also includes a first core positioned in the lumen of the first tubular hoop and a second core positioned in the lumen of the second tubular hoop. Each of the first and second cores has a first end and a second end. The first core is oriented with the first and second ends of the first core positioned away from the split in the first tubular hoop. The second core is oriented with the first and second ends of the second core positioned away from the split in the second tubular hoop. The sleeve includes a first, distal end and a second, proximal end. The first, distal end of the sleeve is coupled to the inner ring of the wound retractor and the second proximal end of the sleeve is coupled to the outer ring of the wound retractor. The outer ring of the wound retractor is substantially rigid and noncompliant.

In one aspect, at least one of the first and second cores includes a substantially rigid, noncompliant wire, while in another aspect at least one of the first and second cores includes a cable. In another aspect, the first circular tube is coupled to the second circular tube through a substantially thin mid-section. In another aspect, the sleeve is made from a thin film. In another aspect, the first and second substantially circular tubes of the outer ring are made of an elastomeric material. In one aspect, the first and second substantially circular tubes are made of a plastic material, while in another aspect the first and second substantially circular tubes are made of a rubber material. In another aspect, the first and second ends of the first core are positioned substantially opposite the first and second ends of the first tubular hoop, and the first and second ends of the second core are positioned substantially opposite the first and second ends of the second tubular hoop. In another aspect, each of the combinations of the first tubular hoop with the first core and the second tubular hoop with the second core functions as an axle about which the outer ring may turn for half a rotation. In one aspect, the first circular tube of the outer ring of the wound retractor is adapted to be rolled outside the second circular tube of the outer ring with the circumference of the first split tubular hoop in the first circular tube expanding to clear the second split tubular hoop in the second circular tube of the outer ring. The second circular tube of the outer ring of the wound retractor is adapted to be rolled outside the first circular tube of the outer ring with the circumference of the second split tubular hoop in the second circular tube expanding to clear the first split tubular hoop in the first circular tube of the outer ring. In one aspect, at least one of the first and second tubular hoops is made of a metallic material, and at least one of the first and second cores is made of a metallic material. In another aspect, at least one of the first and second tubular hoops is made of a composite material, and at least one of the first and second cores is made of a metallic material. In another aspect, at least one of the first and second tubular hoops is made of a metallic material, and at least one of the first and second cores is made of a composite material. In another aspect, at least one of the first and second tubular hoops is made of a composite material, and at least one of the first and second cores is made of a composite material. In one aspect, the first and second substantially circular tubes are parallel to each other, while in another aspect the first and second substantially circular tubes form a helical pattern.

These and other features and advantages of the invention will become more apparent with a discussion of embodiments in reference to the associated drawings.

DETAILED DESCRIPTION

Figure 1:
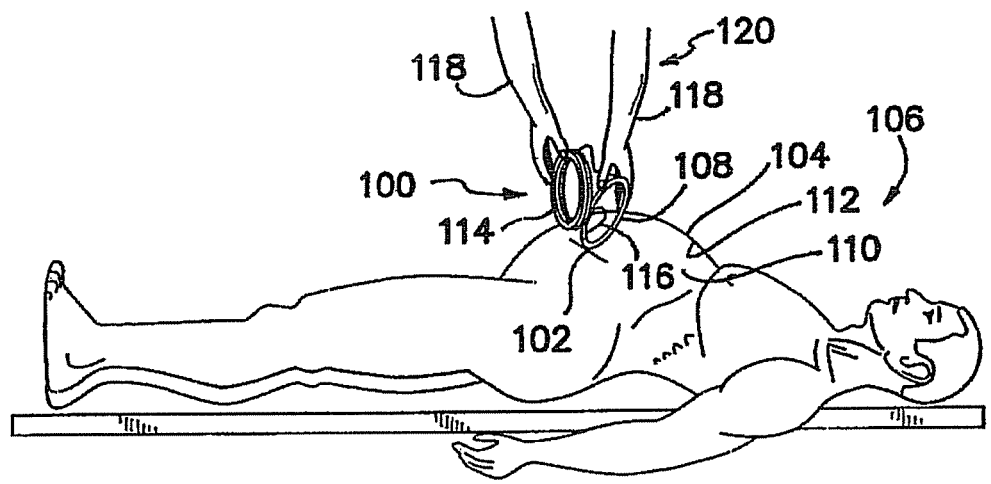
FIG. 1 depicts a technique for placing a surgical wound retractor within an incision.
Figure 2:
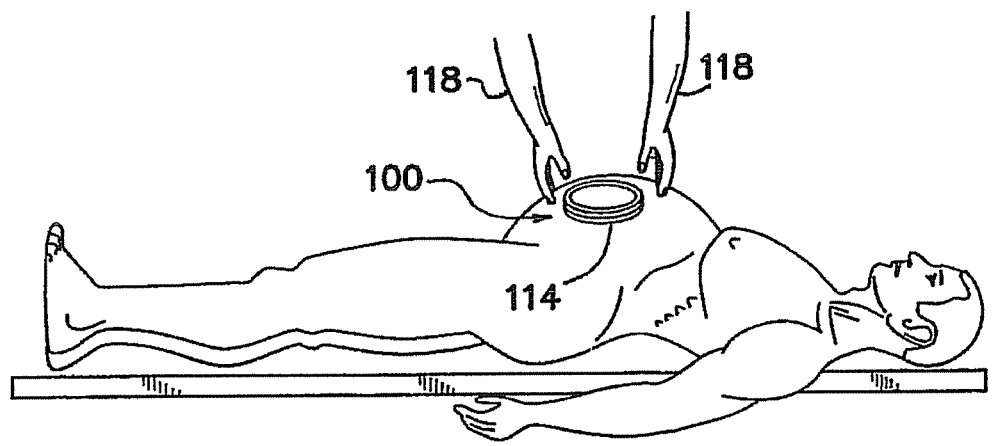
FIG. 2 depicts the surgical wound retractor within an incision.

Referring to the drawings, FIGS. 1 and 2 depict the placement of a wound retractor 100 into an incision 102 made through a body wall 104 of a patient 106. Generally, a first, inner ring 108 is deformed and placed into the incision 102. The first, inner ring 108 is released when it has passed through the body wall 104 of the patient 106 and has reached a body cavity 110 or a reasonably open space. The inner ring 108 typically returns to a substantially circular condition and is subsequently drawn or pulled outwardly and against the inner surface 112 of the body wall 104. Tension between the inner ring 108 and the external components, such as a second, outer ring 114, of the wound retractor 100 is transmitted by means of a substantially cylindrical distensible sleeve 116 that is coupled between the inner ring 108 and the outer ring 114. Tension is increased between the inner and outer rings 108, 114 by winding the sleeve 116 upon the second, outer ring. As the sleeve 116 is shortened, it supplies a retracting or opening force away from the axis of the assembled wound retractor 100. The second, outer ring 114 is easily turned upon itself or inverted by the use of one or two hands 118 of a single user 120 and does not require the use of tools or assistants.

Figure 3:
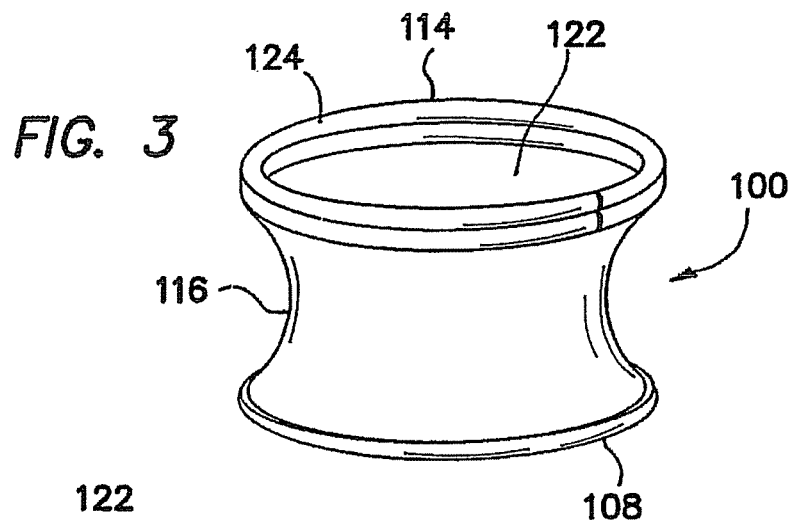
FIG. 3 is a perspective view of an assembled surgical wound retractor.
Figure 4:
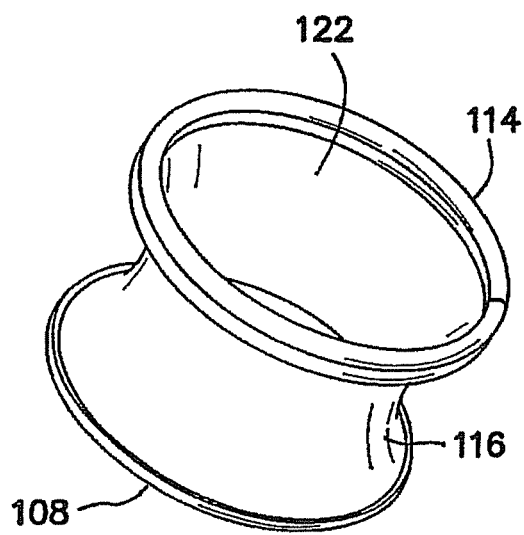
FIG. 4 is a perspective view of an assembled surgical wound retractor of FIG. 3.
Figure 5:
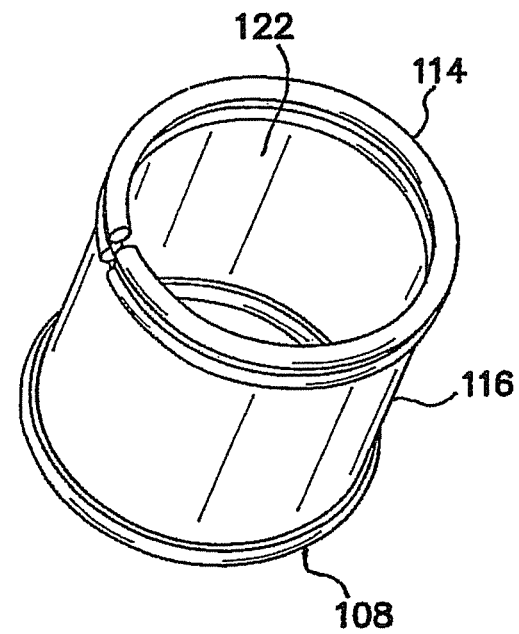
FIG. 5 is a perspective view of an assembled surgical wound retractor having a rigid central support in an outer ring of the wound retractor.
Figure 6:
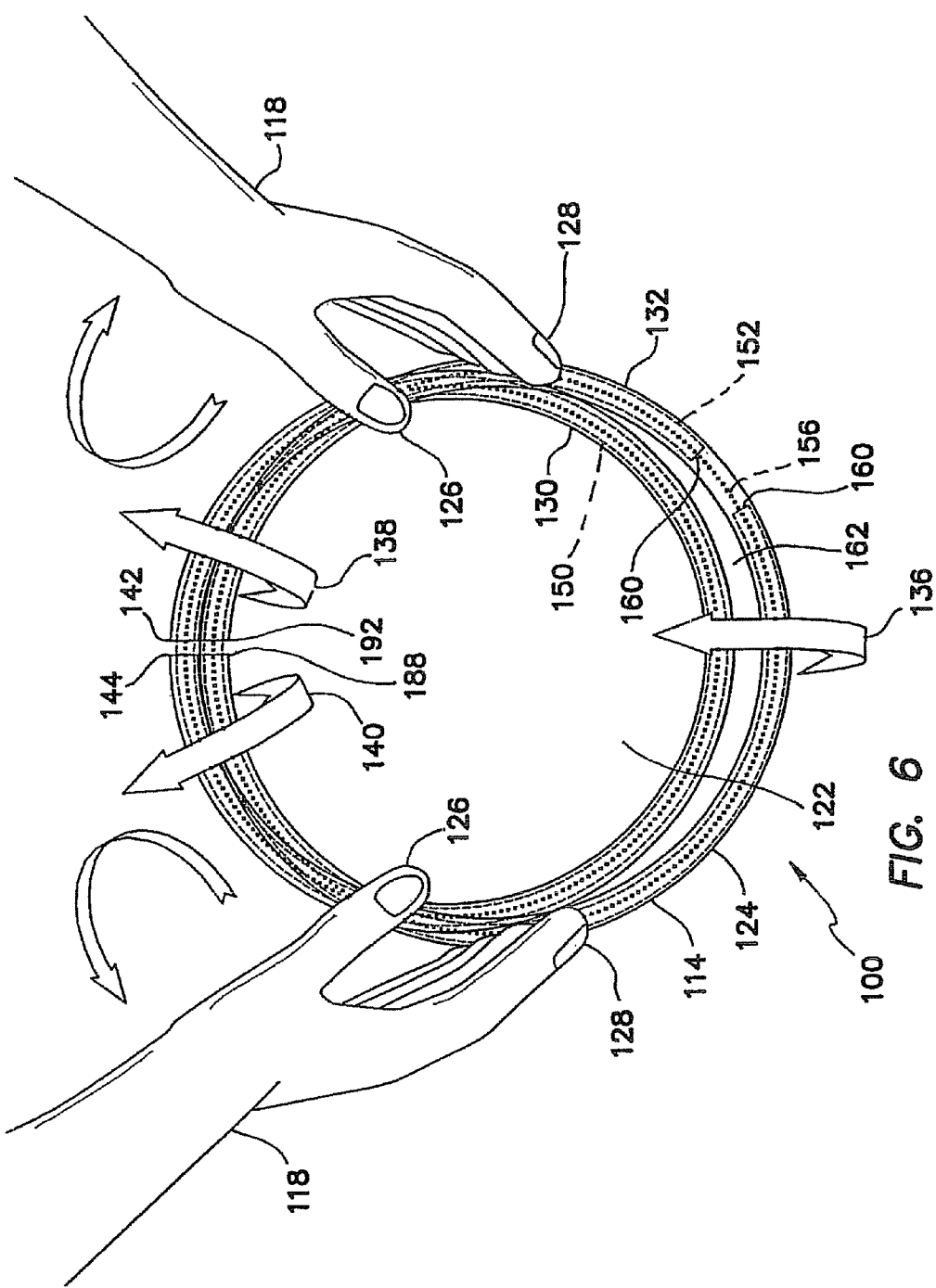
FIG. 6 is a plan view depicting a first step of a technique employed to wind a sleeve of a wound retractor upon the rigid outer ring of the wound retractor.
Figure 7:
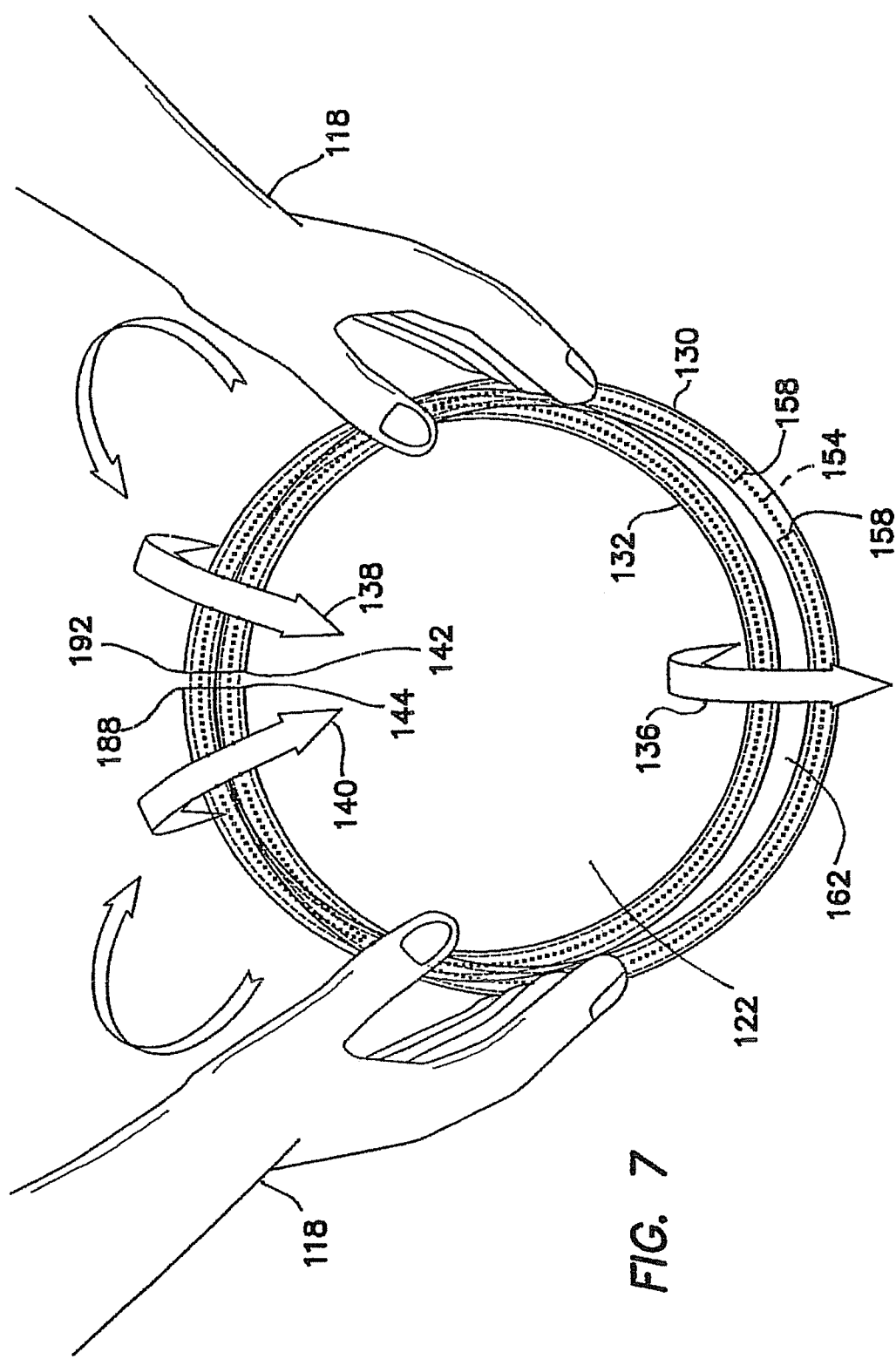
FIG. 7 is a plan view depicting a second step of the technique employed to wind the sleeve of the wound retractor upon the rigid outer ring of the wound retractor.
Figure 8:
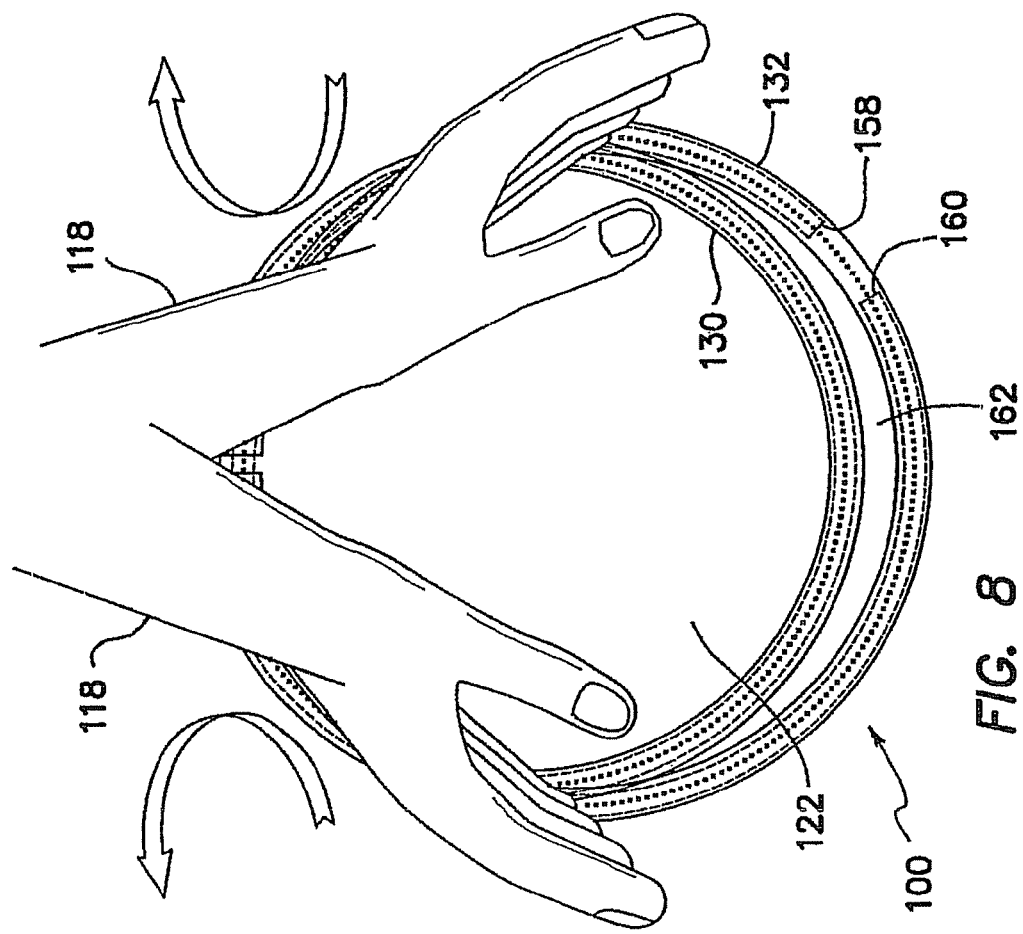
FIG. 8 is a plan view depicting a third step of the technique employed to wind the sleeve of the wound retractor upon the rigid outer ring of the wound retractor.

Referring to FIGS. 3-5, the inner ring 108 of the wound retractor 100 may be circular, oval, elliptical or otherwise shaped to provide easy insertion through the incision 102 (FIG. 1) or opening in the body wall 104 (FIG. 1) and appropriate retraction once in place. The cylindrical sleeve 116 may be made from a thin film and include a first, distal end that is coupled to the inner ring 108. The sleeve 116 has a diameter and a length that forms an open central region 122 that is appropriate for the required retraction and thickness of the body wall 104 (FIG. 1). A second, proximal end of the sleeve 116 is coupled to the second, outer ring 114 that is sized and configured to provide a rigid, noncompliant, substantially circular structure. The rigid, noncompliant outer ring 114 may include an extruded or molded profile that facilitates an inversion step for winding the sleeve 116 upon the outer ring.

Figure 9:
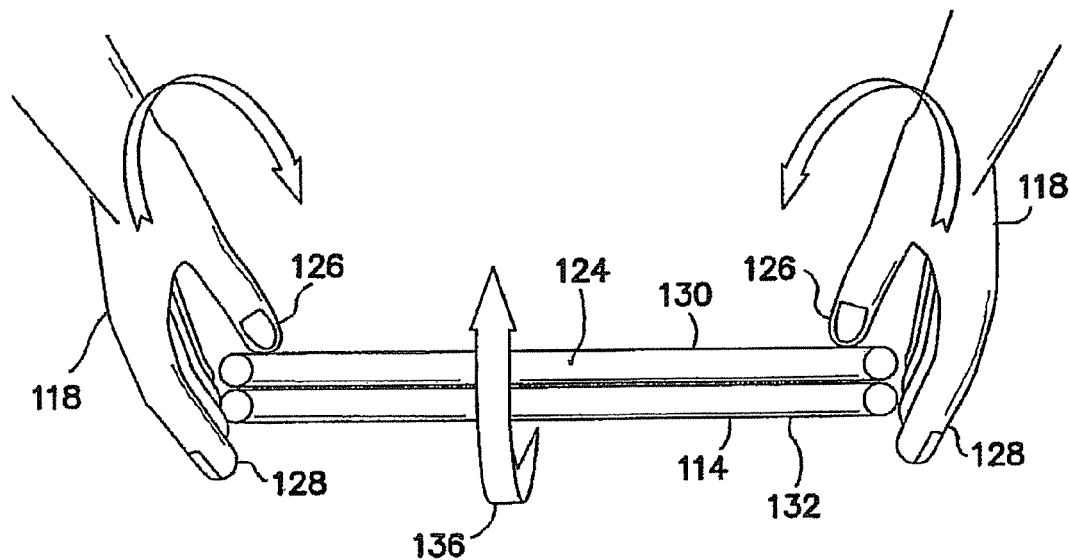
FIG. 9 is a side view depicting the first step of the technique employed to wind the sleeve of the wound retractor upon the rigid outer ring of the wound retractor.
Figure 10:
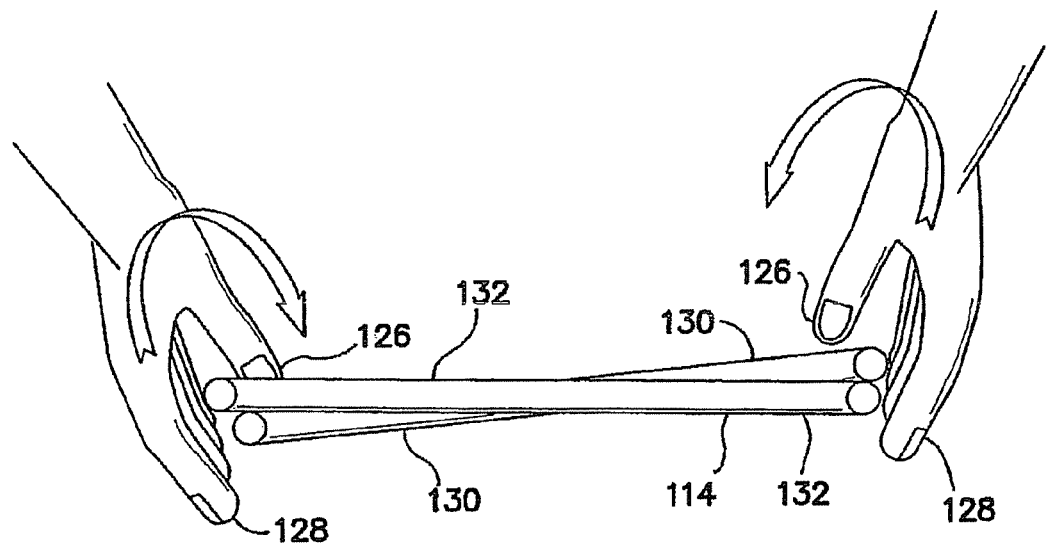
FIG. 10 is a side view depicting the second step of the technique employed to wind the sleeve of the wound retractor upon the rigid outer ring of the wound retractor.
Figure 11:
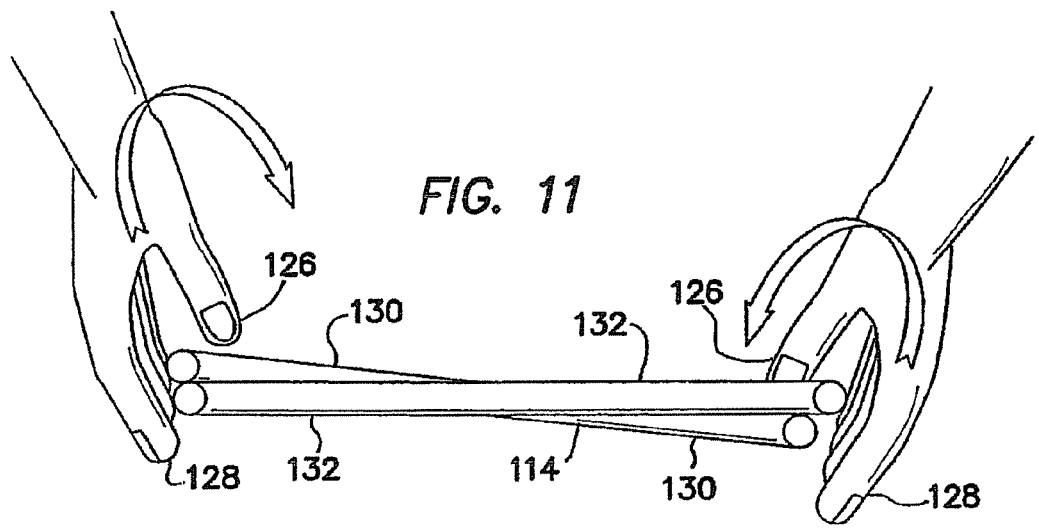
FIG. 11 is a side view depicting the third step of the technique employed to wind the sleeve of the wound retractor upon the rigid outer ring of the wound retractor.
Figure 12:
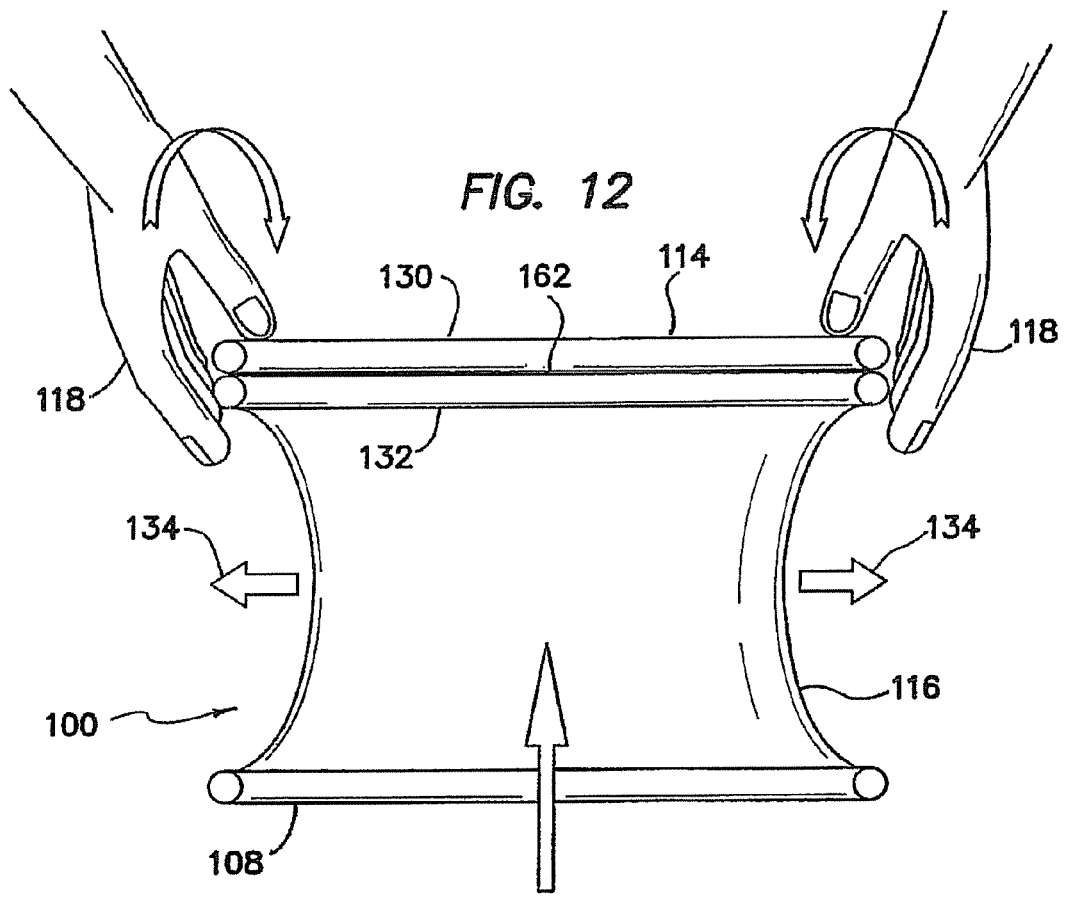
FIG. 12 is a side view of the assembled wound retractor prior to winding the sleeve upon the rigid outer ring.
Figure 13A:
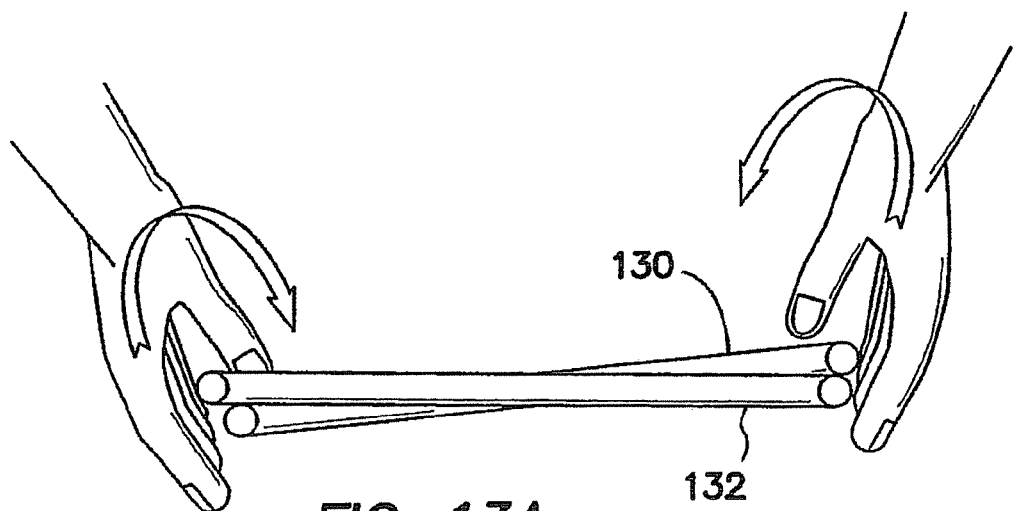
FIGS. 13A-13C are side views depicting the sequence of winding the sleeve upon the rigid outer ring of the wound retractor.
Figure 13B:
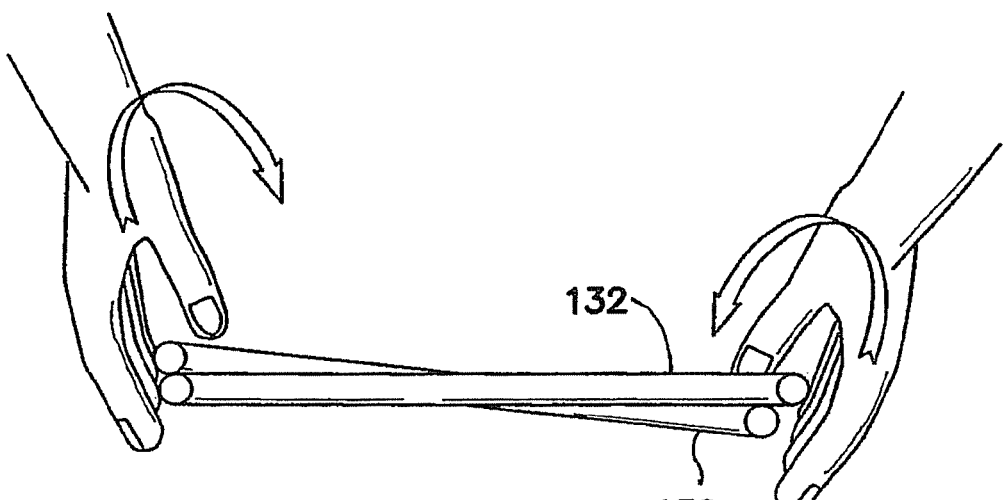
Figure 13C:
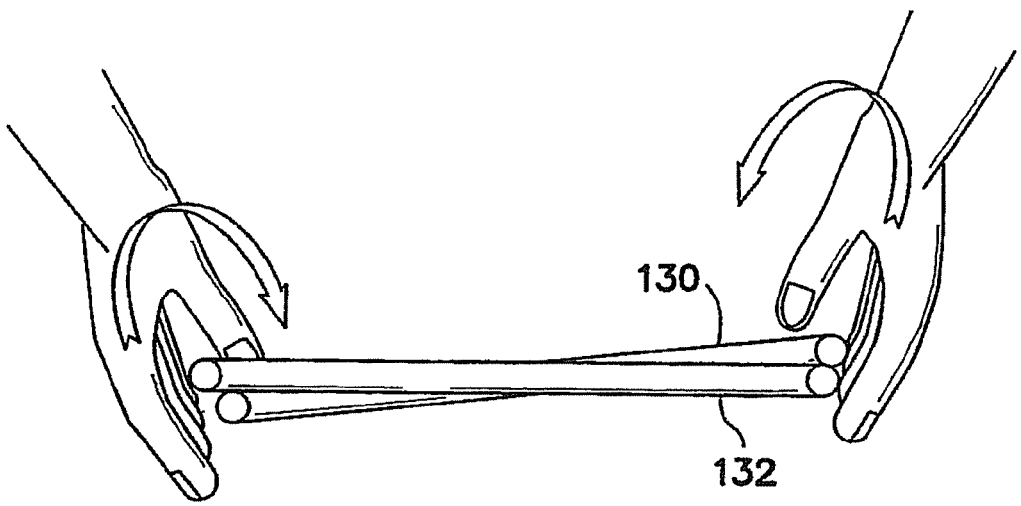
Figure 14A:
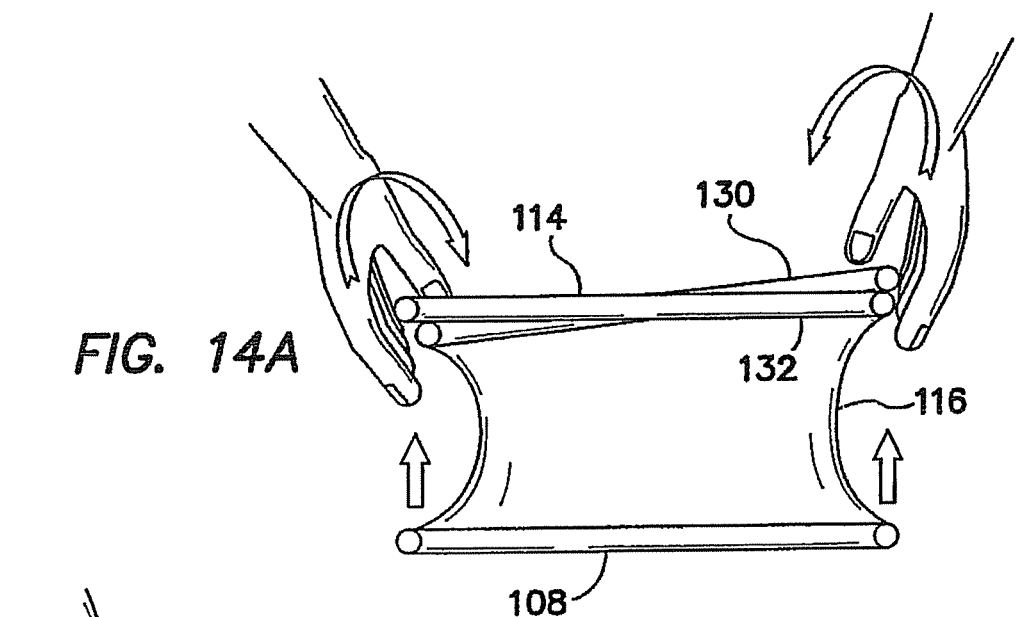
FIGS. 14A-14C are side views depicting the proportions of changes of the length of the sleeve as the winding of the sleeve progresses.
Figure 14B:
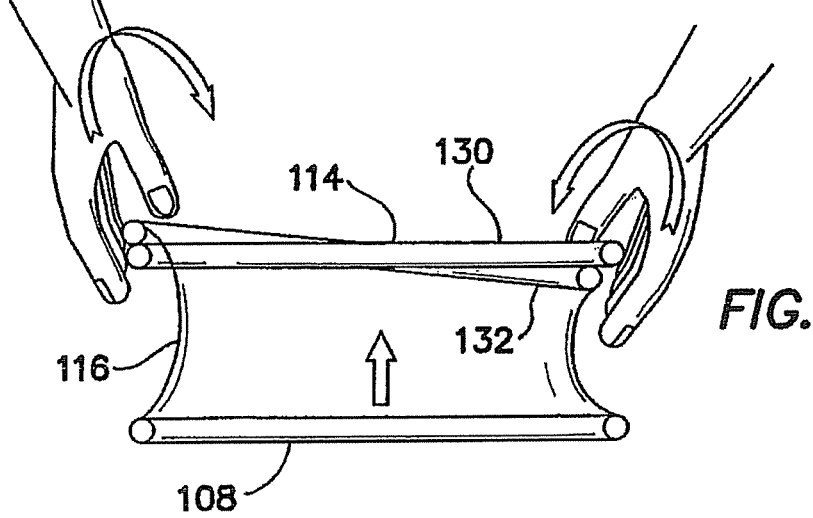
Figure 14C:
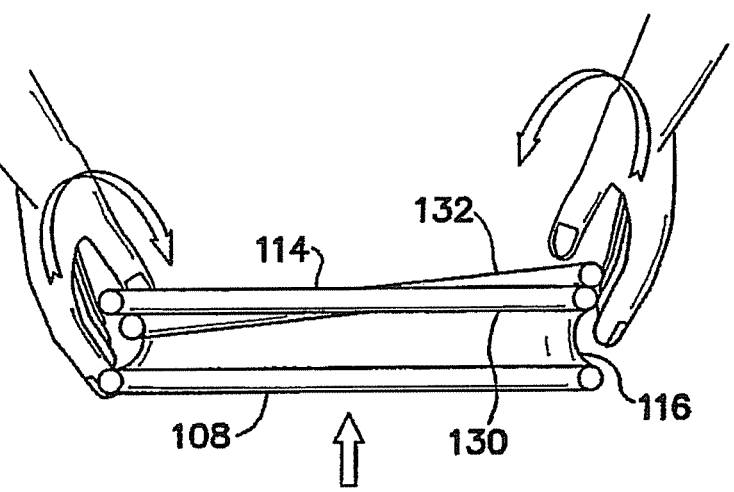
Figure 15:
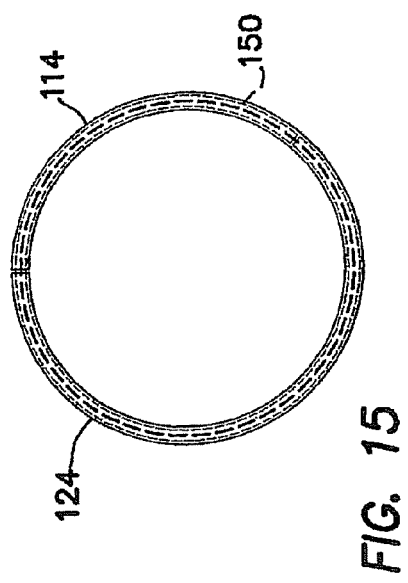
FIG. 15 is a plan view of the rigid outer ring of the wound retractor in a normal at-rest state.
Figure 16:
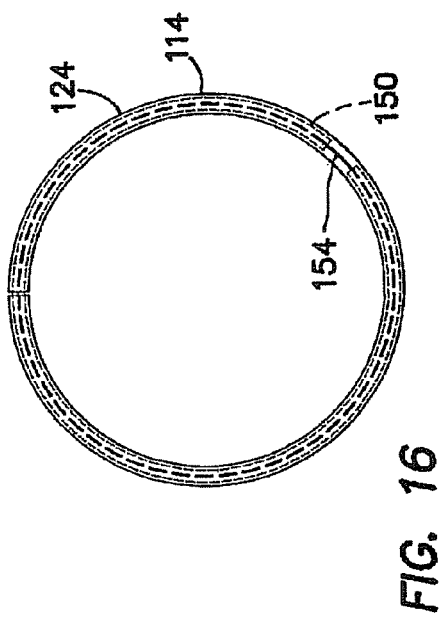
FIG. 16 is a plan view of the rigid outer ring of the wound retractor in an expanded state.
Figure 17:
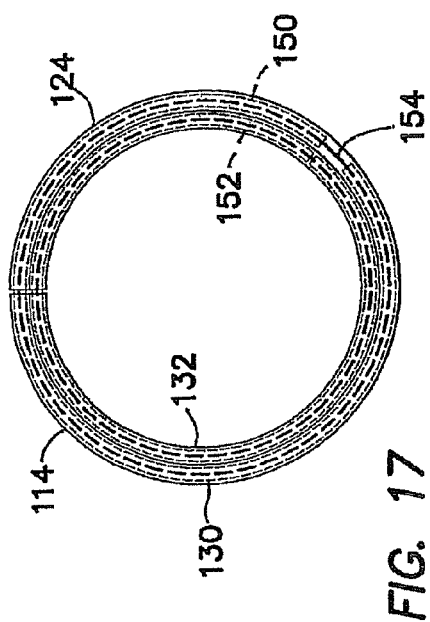
FIG. 17 is a plan view of the rigid outer ring of the wound retractor in a first winding state.
Figure 18:
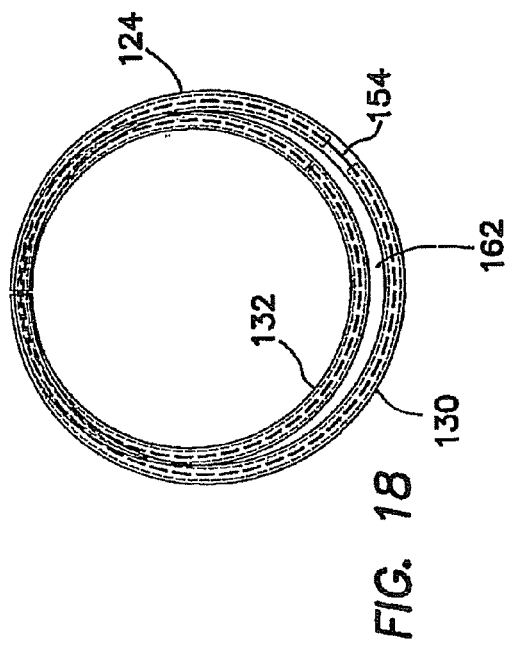
FIG. 18 is a plan view of the rigid outer ring of the wound retractor in a second winding state.
Figure 19:
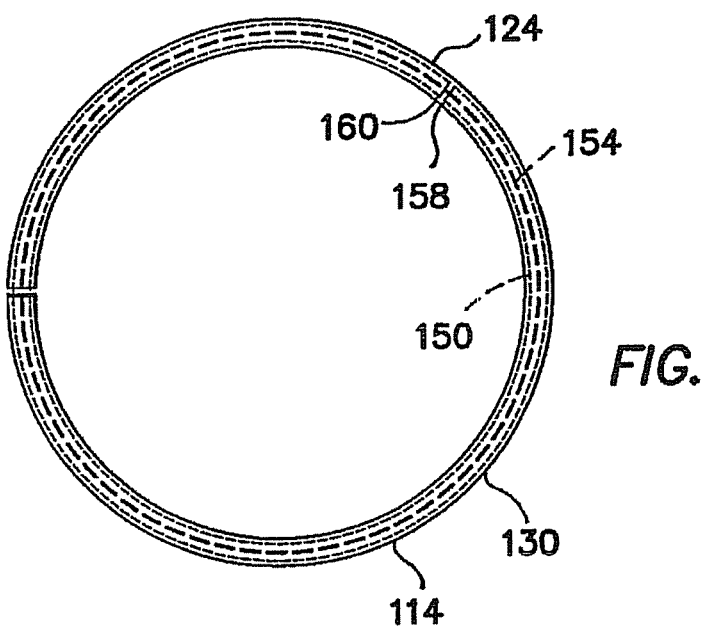
FIG. 19 is a plan view of the rigid outer ring in a normal at-rest state.
Figure 20:
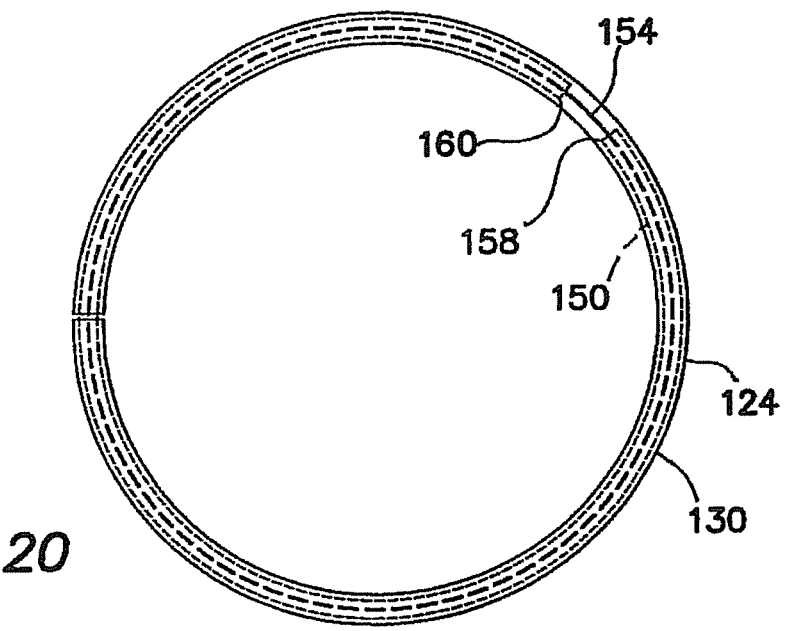
FIG. 20 is a plan view of the rigid outer ring in an expanded state.
Figure 21:
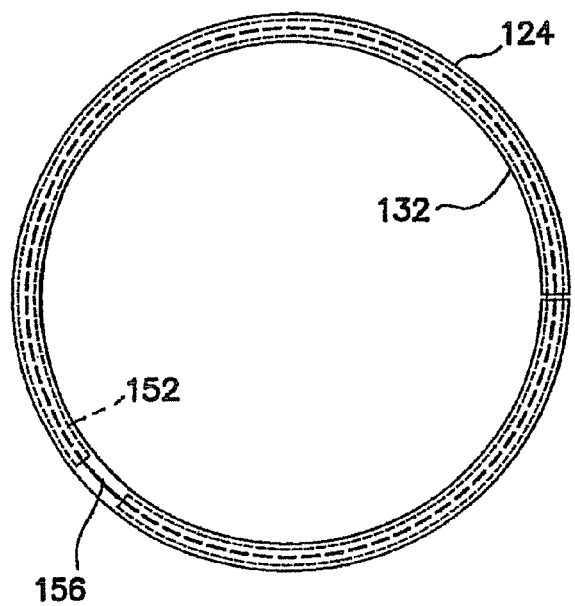
FIG. 21 is a plan view depicting the positioning of a first rigid tube within the outer ring.
Figure 23:
FIG. 23 is a cross sectional view of the rigid outer ring.
Figure 22:
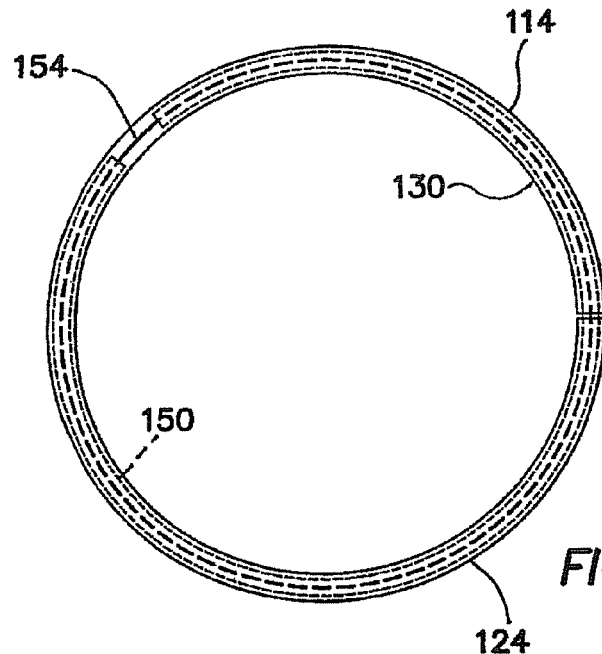
FIG. 22 is a plan view depicting the positioning of a second rigid tube within the outer ring.
Figure 24:
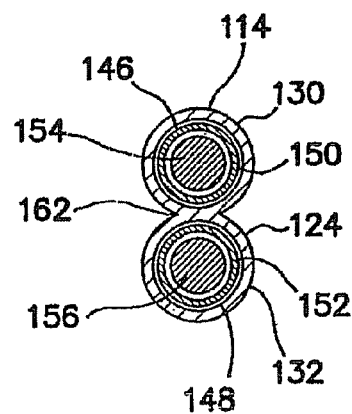
FIG. 24 is a detail cross sectional view of the rigid outer ring.

The process of winding the sleeve 116 upon the outer ring 114 is illustrated in FIGS. 6-14. A user 120 (FIG. 1) grasps the outer ring 114 and rolls it inwardly toward the center of the wound retractor 100. The user 120 may roll the outer ring 114 sequentially or asymmetrically using one hand 118 at a time, or the user may use both hands symmetrically. The outer ring 114 may be rolled over and over several times, resulting in a shortening of the functional length of the sleeve 116 coupled thereto. The outer ring 114 is substantially rigid and noncompliant and, therefore, requires considerable force to invert or roll. An object of the invention is to minimize the force required to invert the outer ring 114 and increase the tension upon the sleeve 116. A very soft plastic or rubber material may be used to make a first circular tube 130 and a second circular tube 132 of a multiple-tube outer cover portion 124 of the outer ring 114, such as a double-tube outer ring or a triple-tube outer ring. The soft material favors traction between the outer ring 114 and the hands 118 of the user 120. The rolling or inverting may, therefore, be accomplished with the thumbs 126 and fingertips 128 of the user 120. As depicted in FIGS. 9 and 12, the first and second circular tubes 130, 132 may be substantially parallel to each other.

The first circular tube 130 of the outer ring 114 rotates through the open central region 122 of the second circular tube 132 of the outer ring, resulting in a first winding of the sleeve 116. The second circular tube 132 of the outer ring 114 may then be rotated through the open central region 122 of the first circular tube 130 of the outer ring, resulting in a second winding of the sleeve 116. These actions may be repeated until appropriate tension is placed upon the sleeve 116 and sufficient retraction 134 (FIG. 12) is applied to the incision 102 (FIG. 1) in the body wall 104. In one aspect, the hands 118 of the user 120 alternately move the first circular tube 130 of the outer ring 114 through the central region 122 of the second circular tube 132 of the outer ring and so on in a first direction (FIG. 6) 136, 138, 140 that results in a winding of the sleeve 116 outwardly and away from the axis of the wound retractor 100. Alternatively, the hands 118 of the user 120 alternately move the first circular tube 130 of the outer ring 114 through the central region 122 of the second circular tube 132 of the outer ring and so on in a second direction (FIG. 7) that results in a winding of the sleeve 116 inwardly toward the axis of the wound retractor 100. The inner ring 108 of the wound retractor 100 is adapted for juxtaposition with the inner surface 112 of the body wall 104 and the outer ring 114 of the wound retractor is adapted for juxtaposition with the outer surface of the body wall. Both the inner ring 108 and the outer ring 114 are adapted for disposition relative to the incision 102 in the body wall 104. The sleeve 116 is adapted to traverse the incision 102 in the body wall 104.

The construction of the rigid, noncompliant outer ring 114 is further detailed in FIGS. 6, 7 and 15-24 where a generally circular structure is shown having a flexible, elastomeric plastic or rubber extrusion or molded elongate body 124 having a first end 142 and a second end 144. The outer ring 115 of the wound retractor 100 also includes at least one lumen. In one aspect, the outer ring 114 of the wound retractor 100 includes a first lumen 146 and a second lumen 148 extending from the first end 142 to the second end 144 through the elongate body 124. This construction generally favors an extrusion manufacturing method.

A rigid, noncompliant metal or plastic tubular hoop 150 extends from the first end 142 of the elongate body to the second end 144 of the elongate body 124. The rigid, noncompliant tubular hoop 150 may be made from a substantially straight tube and bent or formed into an open circular form having a tube diameter slightly smaller than the lumen diameter of the elongate body 124 when it is coupled end to end. More particularly, a first circular rigid, noncompliant tubular hoop 150 is inserted into the first lumen 146 of the elongate body 124. The first tubular hoop 150 includes a split that forms open ends 158 of the first tubular hoop. A second circular rigid, noncompliant tubular hoop 152 is inserted into the second lumen 148 of the elongate body 124. The second tubular hoop 152 includes a split that forms open ends 160 of the second tubular hoop.

A first core 154 may be inserted into the lumen of the first circular rigid, noncompliant tubular hoop 150 and a second core 156 may be inserted into the lumen of the second circular rigid, noncompliant tubular hoop 152. Each of the first and second cores 154, 156 may include a first end and a second end to facilitate insertion into the respective lumens of the first and second tubular hoops 150, 152. At least one of the first and second cores 154, 156 may include a substantially rigid, noncompliant wire or a stranded cable. The first core 154 is advanced through the lumen of the first rigid, noncompliant tubular hoop 150 so that the ends of the core are an appropriate distance away from the open ends 158 thereof (FIG. 7), such as substantially opposite the open ends of the first tubular hoop. The second core 156 is similarly advanced through the lumen of the second rigid, noncompliant tubular hoop 152 so that the ends of the core are an appropriate distance away from the open ends 160 thereof (FIG. 6), such as substantially opposite the open ends of the second tubular hoop. The ends of the first and second cores 154, 156 may be positioned about 180° from the open ends of the rigid, noncompliant circularly formed tubular hoops 150, 152.

The cores 154, 156 stabilize the open ends of the rigid, noncompliant tubular hoops 150, 152 within the lumens 146, 148 of the outer ring 114 so that the open ends of the rigid, noncompliant tubular hoops remain substantially constantly aligned as they open and close in response to the rolling action 136, 138, 140 applied to the outer ring. Each of the combinations of the first tubular hoop 150 with the first core 154 and second tubular hoop 152 with the second core 156 functions as an axle about which the outer ring 114 may turn for half a rotation, or 180°. More particularly, the first circular tube 130 of the outer ring 114 of the wound retractor 100 may be rolled outside the second circular tube 132 of the outer ring with the circumference of the first split tubular hoop 150 in the first circular tube expanding to clear the second split tubular hoop 152 in the second circular tube. Likewise, the second circular tube 132 of the outer ring 114 of the wound retractor 100 may be rolled outside the first circular tube 130 of the outer ring with the circumference of the second split tubular hoop 152 in the second circular tube expanding to clear the first split tubular hoop 150 in the first circular tube.

Referring to FIGS. 23-28, an outer ring 114 is shown including an extruded or molded profile 124 having a first circular tube 130 and a second circular tube 132. The outer ring 114 may include a cross section that resembles the numeral eight (8). The first circular tube 130 and the second circular tube 132 are axially spaced from each other and are coupled together through a substantially thin mid-section 162. The outer ring 114 includes the first lumen 146 in the first circular tube 130 and the second lumen 148 in the second circular tube 132. A first rigid, noncompliant tubular hoop 150 having a split that forms open ends 158 may be inserted into the first lumen 146 of the outer ring 114 and a second rigid, noncompliant tubular hoop 152 having a split that forms open ends 160 may be inserted into the second lumen 148 of the outer ring. A rigid, noncompliant core 154, 156, such as a wire hoop or a loop of stranded cable, is inserted into the lumen of each of the rigid, noncompliant tubular hoops 150, 152 and advanced until the ends of the respective core are positioned well within the rigid, noncompliant tubular hoops. The first and second cores 154, 156 serve to maintain alignment of the two opposed ends of the rigid, noncompliant tubular hoops 150, 152. The tubular hoops 150, 152 containing cores 154, 156 are subsequently advanced to positions well within the lumens 146, 148 of the outer ring 114. More particularly, the first tubular hoop 150 is oriented such that the open ends 158 of the first tubular hoop are positioned away from the first and second ends 142, 144 of the first circular tube 130 of the outer ring 114, such as substantially opposite the first and second ends of the first circular tube. Similarly, the second tubular hoop 152 is oriented such that the open ends 160 of the second tubular hoop are positioned away from the first and second ends 188, 192 of the second circular tube 132 of the outer ring 114, such as substantially opposite the first and second ends of the first circular tube.

Figure 25:
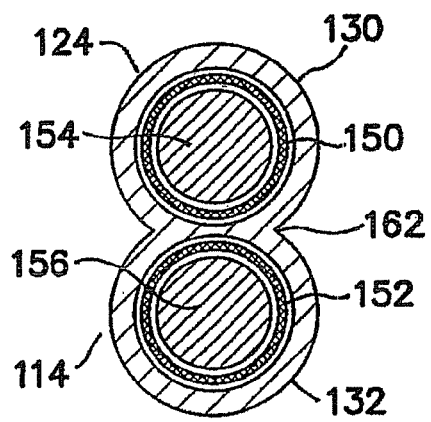
FIG. 25 is a cross sectional view of a rigid outer ring having two portions.

Referring to FIG. 25, the outer ring 114 may include a highly resilient outer portion 124, a first rigid, noncompliant composite tubular hoop 150, a second rigid, noncompliant composite tubular hoop 152, a first core 154, such as a rigid, noncompliant metallic member and a second core 156, such as a rigid, noncompliant metallic central member. The rigid, noncompliant tubular hoops 150, 152 are sized and configured to maintain a generally circular shape relative to the central axis of the wound retractor 100 (FIG. 1). In addition, the cores 154, 156 within the tubular hoops 150, 152 provide additional rigidity and also maintain alignment of the ends 158, 160 of the tubular hoops. The rigid, noncompliant composite tubular hoops 150, 152 may be made from composites that are well known in the art, such as phenolic, polycarbonate, polyester or other plastics filled with glass fiber, carbon fiber or other well known materials.

Figure 26:
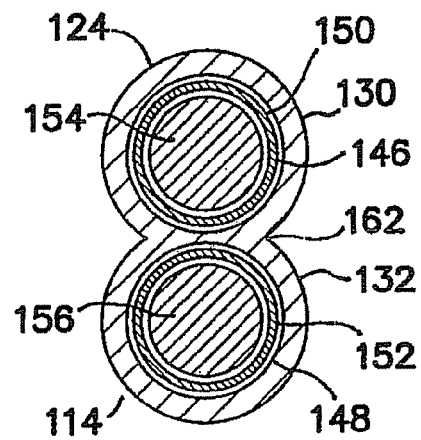
FIG. 26 is a cross sectional view of a rigid outer ring having two portions.

Referring to FIG. 26, the outer ring 114 may include a highly resilient outer portion 124, a first rigid, noncompliant metallic tubular hoop 150, a second rigid, noncompliant metallic tubular hoop 152, a first core 154, such as a rigid, noncompliant metallic member, and a second core 156, such as a rigid, noncompliant metallic member. The rigid, noncompliant tubular hoops 150, 152 are sized and configured to maintain a generally circular shape relative to the central axis of the wound retractor 100 (FIG. 1). In addition, the cores 154, 156 within the rigid, noncompliant tubular hoops 150, 152 provide additional rigidity and also maintain alignment of the ends 158, 160 of the central tubular hoops.

Figure 27:
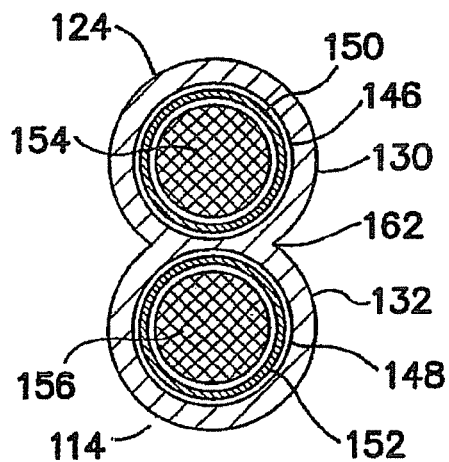
FIG. 27 is a cross sectional view of a rigid outer ring having two portions.

Referring to FIG. 27, the outer ring 114 may include a highly resilient outer portion 124, a first rigid, noncompliant metallic tubular hoop 150, a second rigid, noncompliant metallic tubular hoop 152, a first core 154, such as a substantially rigid, noncompliant composite member and a second core 156, such as a substantially rigid, noncompliant composite member. The rigid, noncompliant tubular hoops 150, 152 are sized and configured to maintain a generally circular shape relative to the central axis of the wound retractor 100 (FIG. 1). In addition, the composite cores 154, 156 within the rigid, noncompliant tubular hoops 150, 152 provide additional rigidity and also maintain alignment of the ends 158, 160 of the central tubular hoops. The rigid, noncompliant composite cores 154, 156 may be made from composites that are well known in the art, such as phenolic, polycarbonate, polyester or other plastics filled with glass fiber, carbon fiber or other well known materials.

Figure 28:
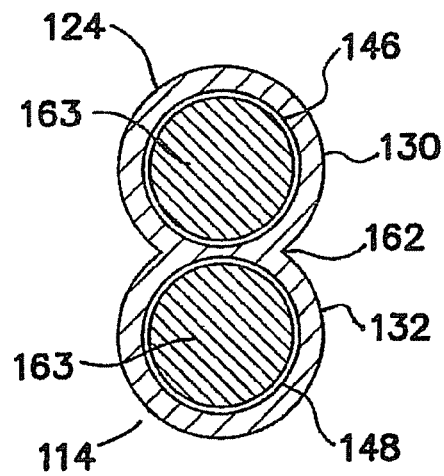
FIG. 28 is a cross sectional view of a rigid outer ring having two portions.

Referring to FIG. 28, the outer ring 114 may include a highly resilient outer portion 124 and solid hoops 163 within the lumens 146, 148 of the external retention member.

Figure 29:
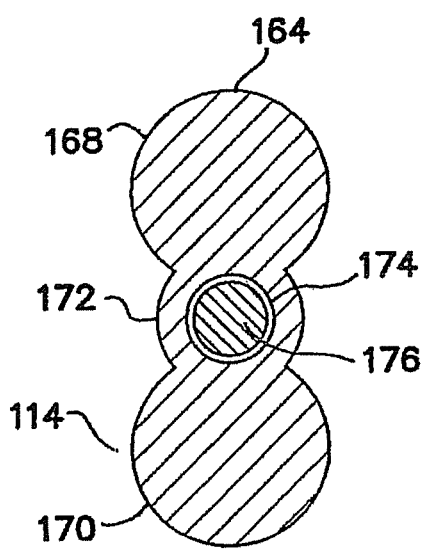
FIG. 29 is a cross sectional view of the rigid outer ring having three portions with a single lumen that is positioned in the center portion.

Referring to FIG. 29, the outer ring 114 may include a highly resilient extruded or molded outer portion 164 having a first circular tube 168, a second circular tube 170 and a third circular tube 172. The first circular tube 168 is a large diameter cord. The second circular tube 170 is a large diameter cord that is separated from the first circular tube 168 by a third, smaller central circular tube 172 that has a lumen 174 therethrough. Alternatively, the three cords or circular tubes 168, 170, 172 may all be substantially the same size. The first, second and third circular tubes 168, 170, 172 are substantially coaxially aligned and each includes a substantially annular axis of substantially equal diameter. The first and second circular tubes or cords 168, 170 cooperate to provide a detent or snap-over as the first and second cords are sequentially rolled over the third circular tube 172. The lumen 174 of the central, third circular tube portion 172 is supplied with a rigid, noncompliant hoop 176 that is constructed from a length of material that has been formed to substantially the diameter of the wound retractor 100. The rigid, noncompliant hoop 176 functions as an axle.

Figure 30:
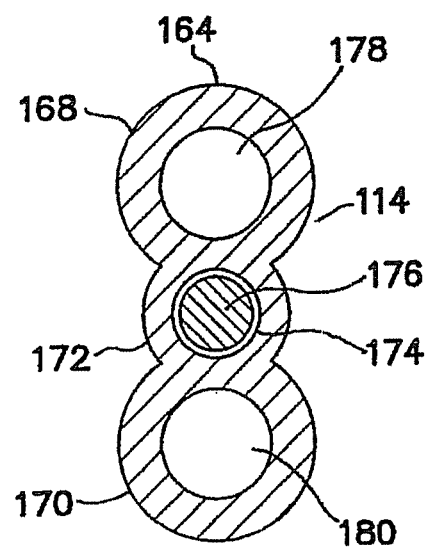
FIG. 30 is a cross sectional view of the rigid outer ring having three portions with a lumen in each of the three portions.

Referring to FIG. 30, the outer ring 114 may include a moderately resilient extruded or molded outer portion 164 having a first circular tube 168, a second circular tube 170 and a third circular tube 172. The first circular tube 168 is a large diameter cord having a lumen 178 therethrough. The second circular tube 170 is a large diameter cord having a lumen 180 therethrough and is separated from the first circular tube 168 by the third, smaller circular tube 172 that has a lumen 174 therethrough. Alternatively, the three circular tubes cords 168, 170, 172 may all be substantially the same size. The first, second and third circular tubes 168, 170, 172 are substantially coaxially aligned and each includes a substantially annular axis of substantially equal diameter. The first and second circular tubes or cords 168, 170 cooperate to provide a detent or snap-over as the cords are sequentially rolled over the third circular tube 172. The lumen 174 of the third circular tube 172 is supplied with a rigid, noncompliant hoop 176 that is constructed from a length of material, such as a metallic material, that has been formed to substantially the diameter of the circular retractor 100. The rigid, noncompliant hoop 176 functions as an axle.

Figure 31:
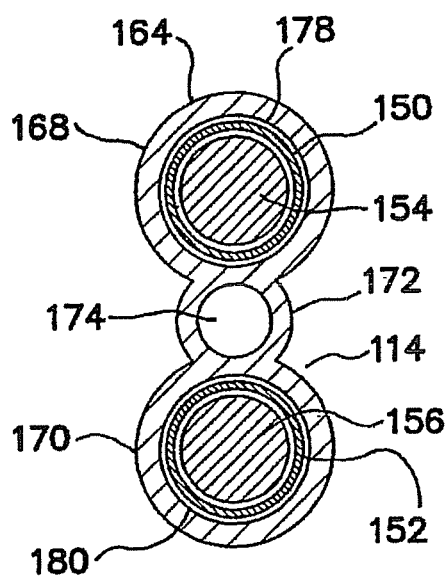
FIG. 31 is a cross sectional view of the rigid outer ring having three portions with a lumen in each of the three portions.

Referring to FIG. 31, the outer ring 114 may include a highly resilient extruded or molded outer portion 164 having a first circular tube 168, a second circular tube 170 and a third circular tube 172. The first circular tube 168 is a large diameter cord having a lumen 178 therethrough. The second circular tube 170 is a large diameter cord having a lumen 180 therethrough and is separated from the first circular tube 168 by the third, smaller circular tube 172 that has a lumen 174 therethrough. Alternatively, the three circular tubes or cords 168, 170, 172 may all be substantially the same size. The first, second and third circular tubes 168, 170, 172 are substantially coaxially aligned and each includes a substantially annular axis of substantially equal diameter. The first and second circular tubes or cords 168, 170 cooperate to provide a detent or snap-over as the cords are sequentially rolled over the third circular tube 172. The lumen 174 of the third circular tube 172 is configured to remain hollow and unfilled. The lumens 178, 180 of the first and second circular tubes are supplied with rigid metallic first and second tubular hoops 150, 152 therein, respectively, that contain rigid, first and second cores 154, 156, such as noncompliant circular wires. The hollow third circular tube 172 provides additional resilience that allows the first and second circular tubes 168, 170 to pass through each other.

Figure 32:
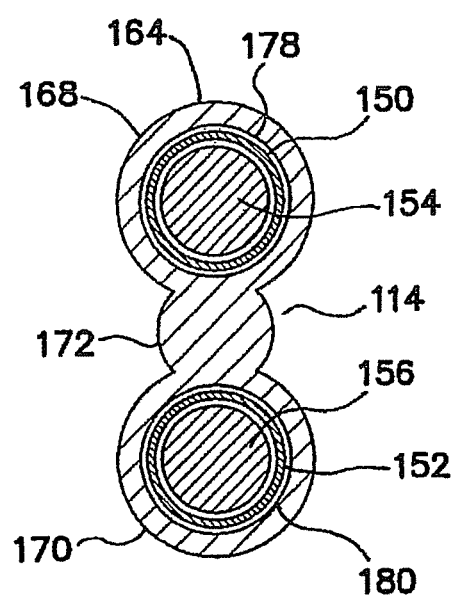
FIG. 32 is a cross sectional view of the rigid outer ring having three portions with two lumens with the lumens being positioned in the outer portions.

Referring to FIG. 32, the outer ring 114 may include a highly resilient extruded or molded outer portion 164 having a first circular tube 168, a second circular tube 170 and a third circular tube 172. The first circular tube 168 is a large diameter cord having a lumen 178 therethrough. The second circular tube 170 is a large diameter cord having a lumen 180 therethrough and is separated from the first circular tube 168 by a third, smaller circular tube 172 that has no lumen therethrough. Alternatively, the three circular tubes or cords 168, 170, 172 may all be substantially the same size. The first, second and third circular tubes 168, 170, 172 are substantially coaxially aligned and each includes a substantially annular axis of substantially equal diameter. The first and second circular tubes or cords 168, 170 cooperate to provide a detent or snap-over as the cords are sequentially rolled over the third circular tube 172. The cord of the third circular tube 172 is solid. The lumens 178, 180 of the first and second circular tubes 150, 152 are supplied with rigid, metallic first and second tubular hoops 150, 152, respectively, therein that contain cores 154, 156, such as rigid, noncompliant circular wires. The solid third circular tube 172 provides a resilient axle that allows the first circular tube 168 and the second circular tube 170 to pass through each other.

Figure 33:
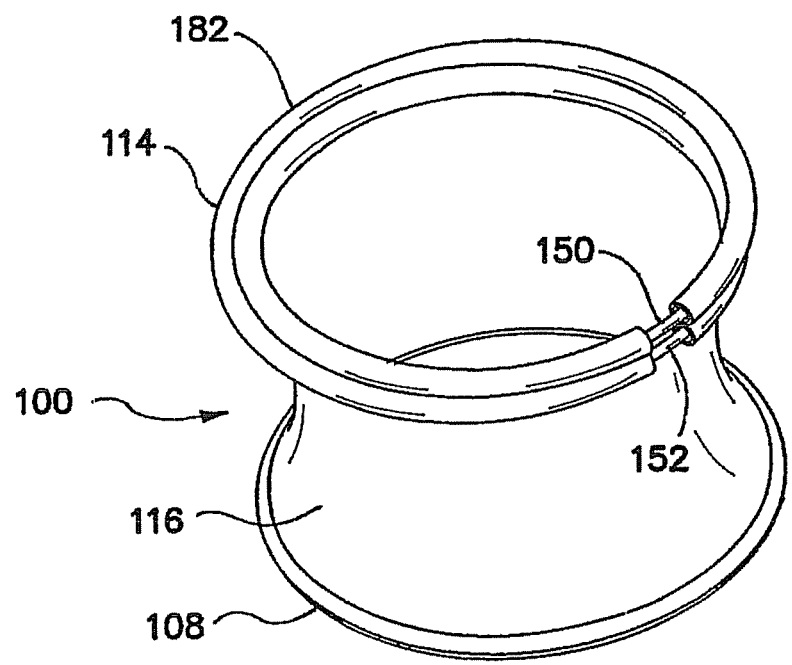
FIG. 33 is a perspective view of an assembled wound retractor having a twisted, rigid outer ring.
Figure 35:
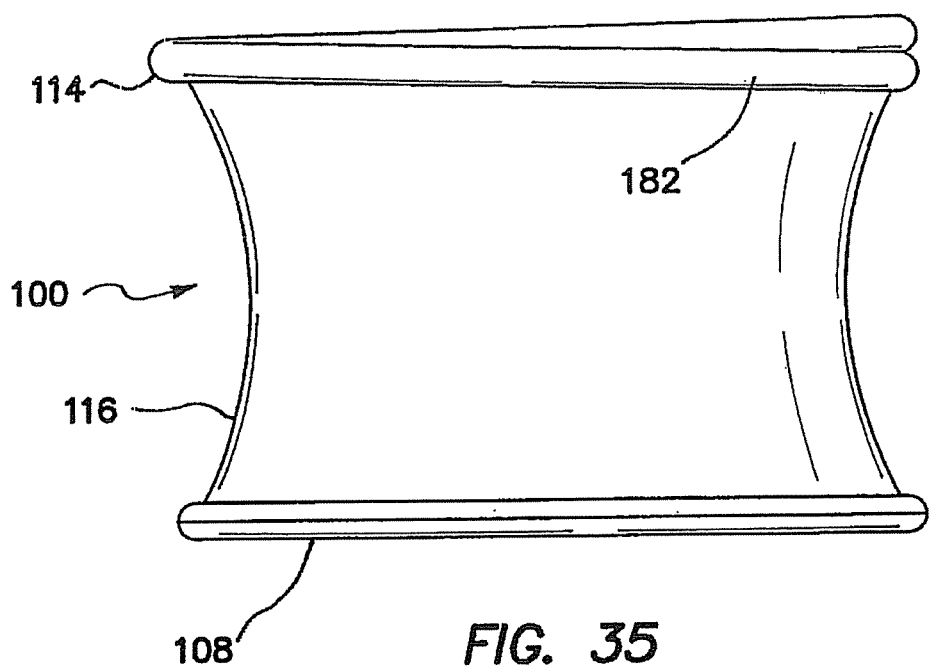
FIG. 35 is a side view of the wound retractor of FIG. 33.
Figure 34:
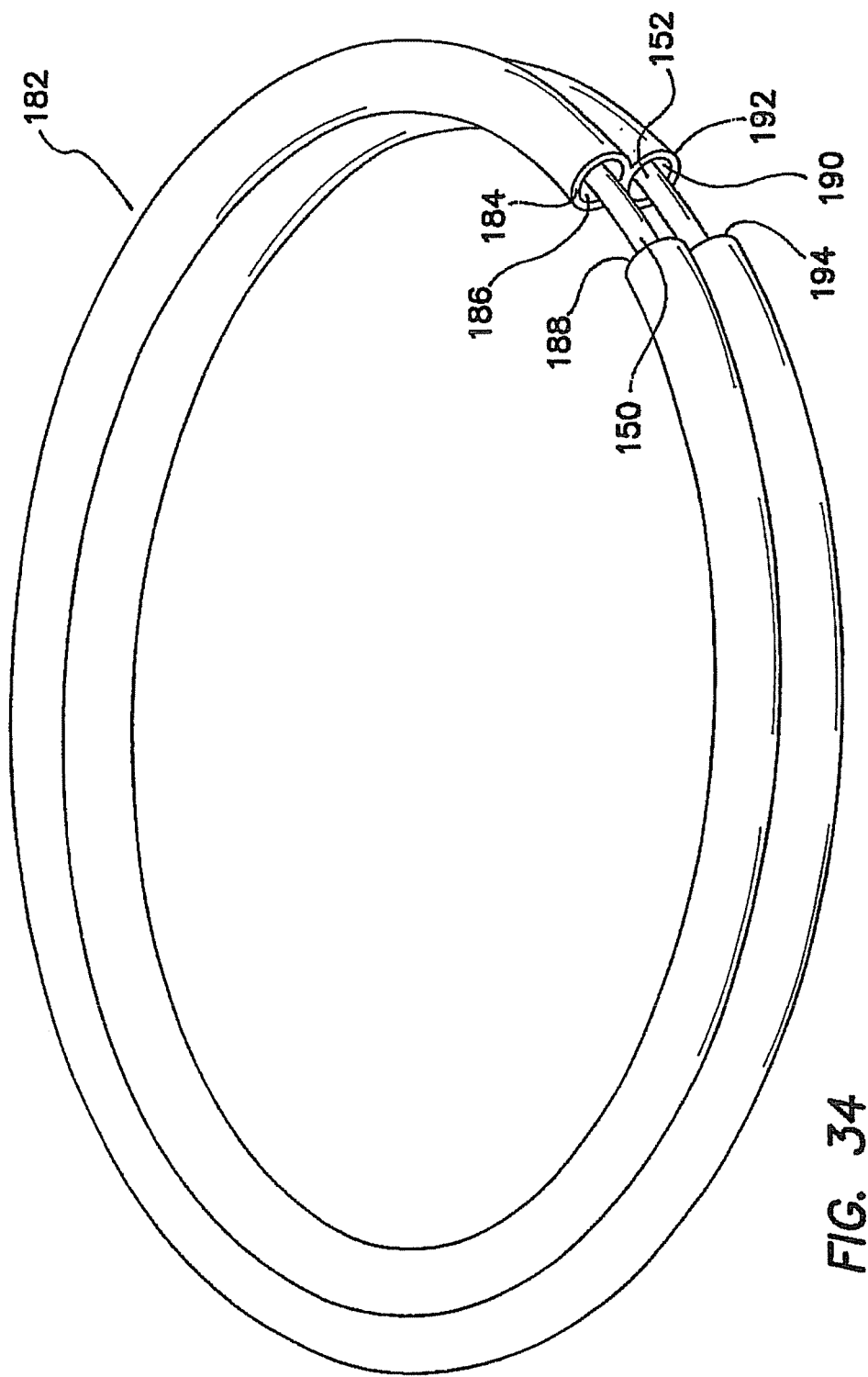
FIG. 34 is a perspective view of the outer ring of the wound retractor of FIG. 33.
Figure 36:
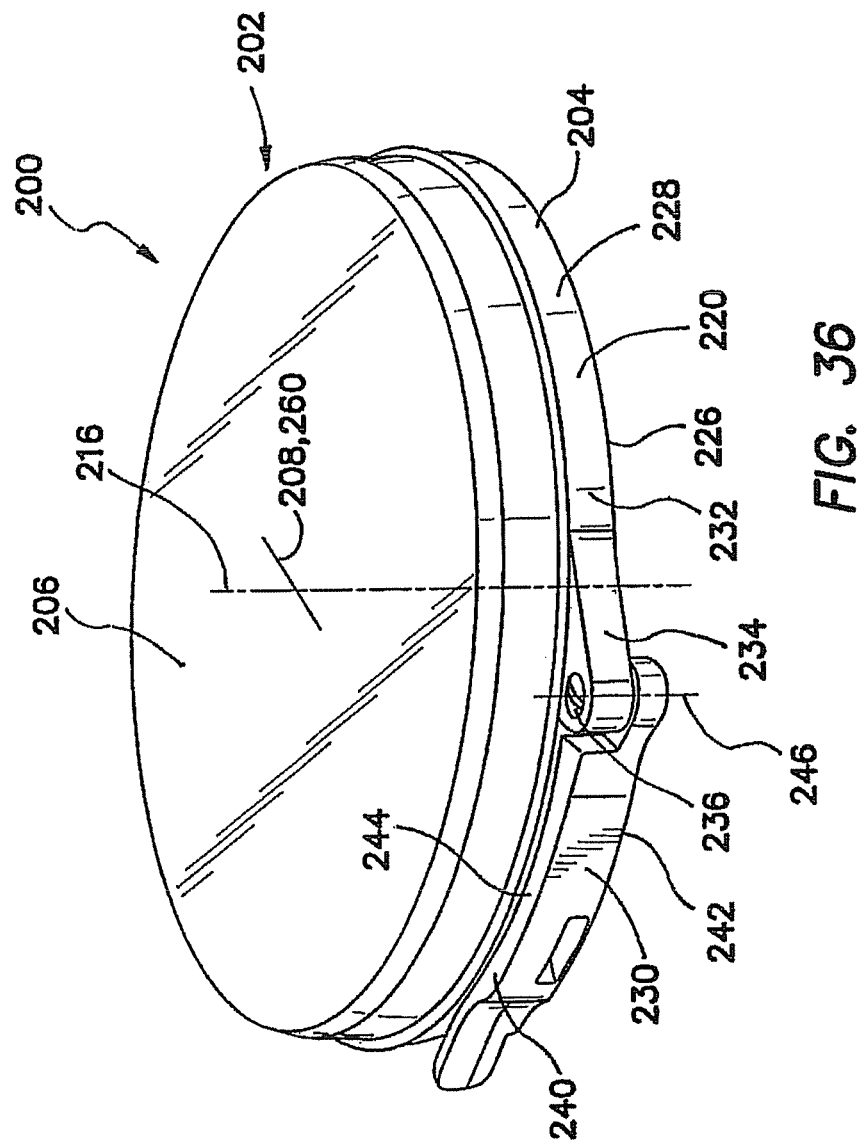
FIG. 36 is a top perspective view of a gel cap having a lever for coupling the gel cap to the outer ring of a wound retractor.

Referring to FIGS. 33-35, the wound retractor 100 may include a first, inner ring 108, a second, outer ring 114, and a sleeve 116 coupling the inner ring to the outer ring. The inner ring 108 may be sized and configured to be deformed and placed through the incision 102 in the body wall 104 and subsequently into the body cavity 110. The sleeve 116 extends through the incision 102 in the body wall 104 and is coupled to the second, outer ring 114 that is sized and configured to be inverted upon itself or rolled to wind the sleeve 116 upon the second, outer ring. The outer ring 114 may include a helical rigid, noncompliant element having a shape similar to a Mobius strip. The helical outer ring 114 may be formed by twisting an extruded or molded element, such as a dual-lumen element 182, so that the first end 184 of the first lumen 186 communicates with the second end 188 of the second lumen 190 and the first end 192 of the second lumen 190 communicates with the second end 194 of the first lumen 186.

The ends 184, 188, 192, 194 of the extruded or molded form 114 are not joined together. A first split tubular hoop 150 is inserted into the first end 184 of the first lumen 186 and advanced until it exits the second end 194 of the first lumen where it is then inserted into the first end 192 of the second lumen 190. A first core 154, such as a rigid, noncompliant wire or a cable may then be inserted into the first tubular hoop 150 and advanced until the ends of the first core are well within the solid portion of the first tubular hoop, such as substantially opposite the ends 184, 186 of the first tubular hoop. The ends of the first core 154 may be separated from the ends of the first rigid, noncompliant tubular hoop 150 by about 180°. The first tubular hoop 150 and first core 154 are then advanced within the first lumen 186 of the extruded or molded element to a point distant from the first and second ends 184, 188 of the twisted circular form 114. A second rigid, noncompliant tubular hoop 152 and a second core 156 are inserted into the first end 192 of the second lumen 190 of the extruded or molded element and advanced as described above. The assembly, which forms an outer ring 114 in the form of a twisted external rigid, noncompliant outer ring, may be inverted or rolled to wind the sleeve 116 upon the outer ring. The helical orientation of the rigid, noncompliant outer ring 114 avoids an extreme detent or snap-over associated with two discrete rigid, noncompliant portions that must pass through each other in a rolling or inverting motion to wind the sleeve 116 upon the rigid, noncompliant outer ring.

Referring to FIGS. 36-45, a gel cap 202 includes a cap ring 204 that couples to the outer ring 114 of the wound retractor 100 and a gel pad 206 coupled to the cap ring. The gel pad 206 is made of a gel material and includes an access portion 208 or passage through the gel for providing a passage from external the body to the body cavity 110. In one aspect, the access portion 208 may include a plurality of intersecting dead-end slits 260, 262. The access portion 208 forms an instrument seal in the presence of an instrument, such as the arm of a surgeon, inserted therethrough and a zero seal in the absence of an instrument inserted therethrough.

Figure 37:
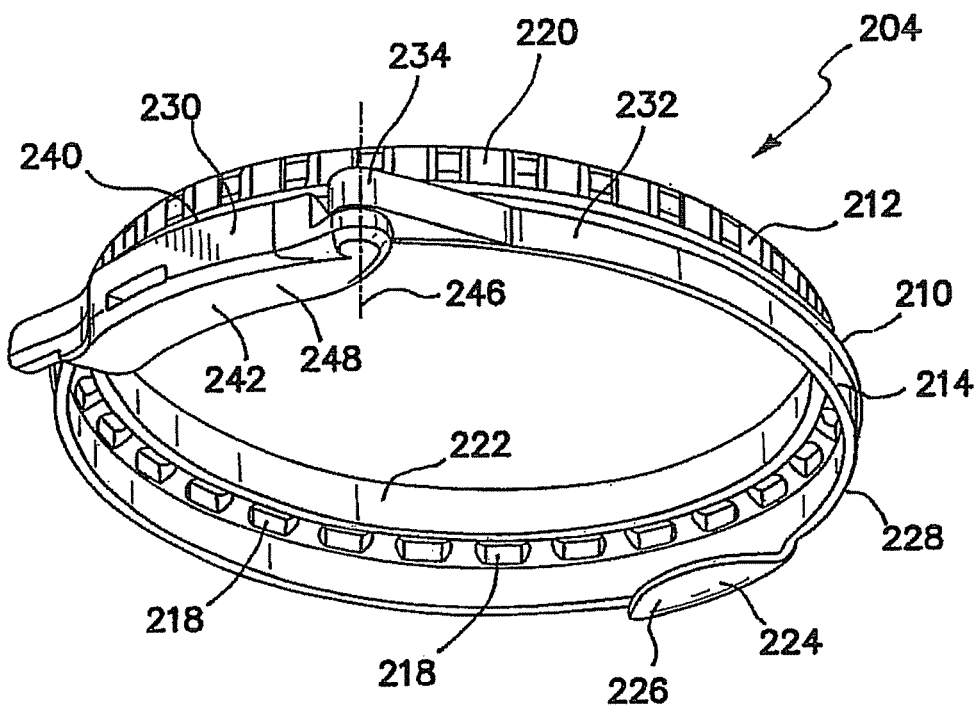
FIG. 37 is a bottom perspective view of a cap ring of the gel cap of FIG. 36.
Figure 38:
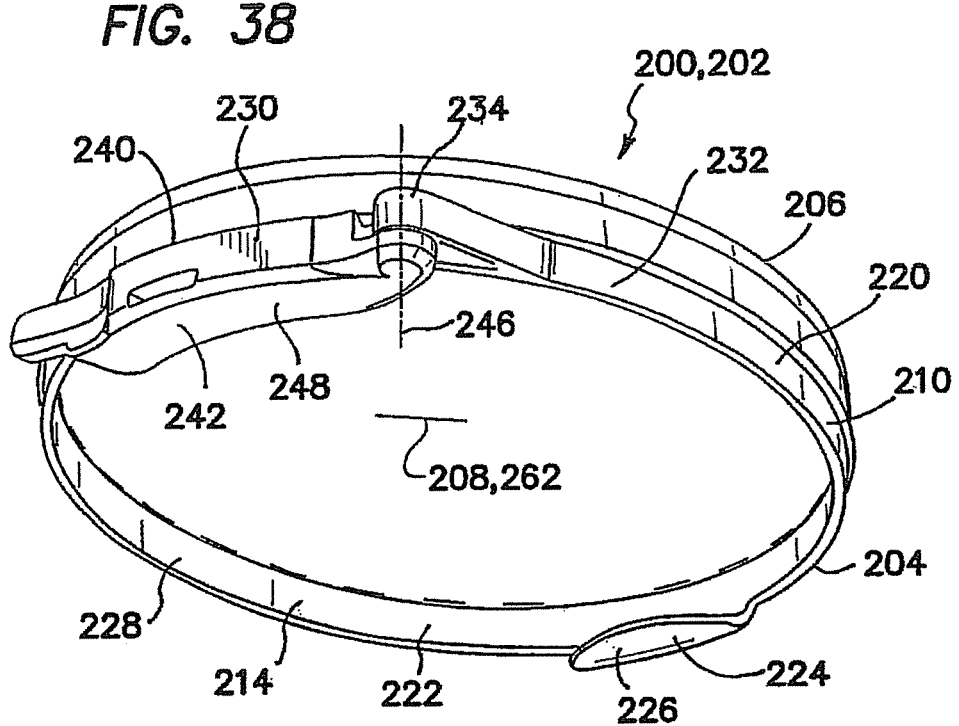
FIG. 38 is a bottom perspective view of the gel cap of FIG. 36.
Figure 39:
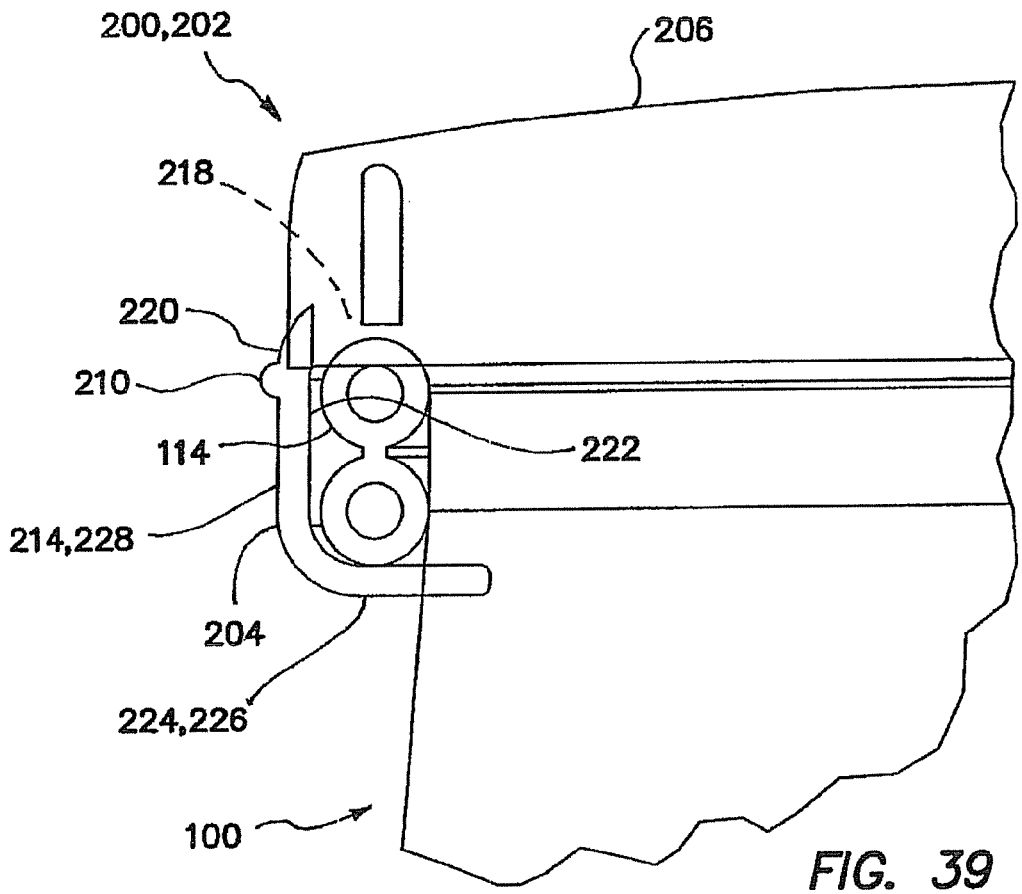
FIG. 39 is a partial section view of the gel cap of FIG. 36 coupled to the outer ring of the wound retractor.
Figure 40:
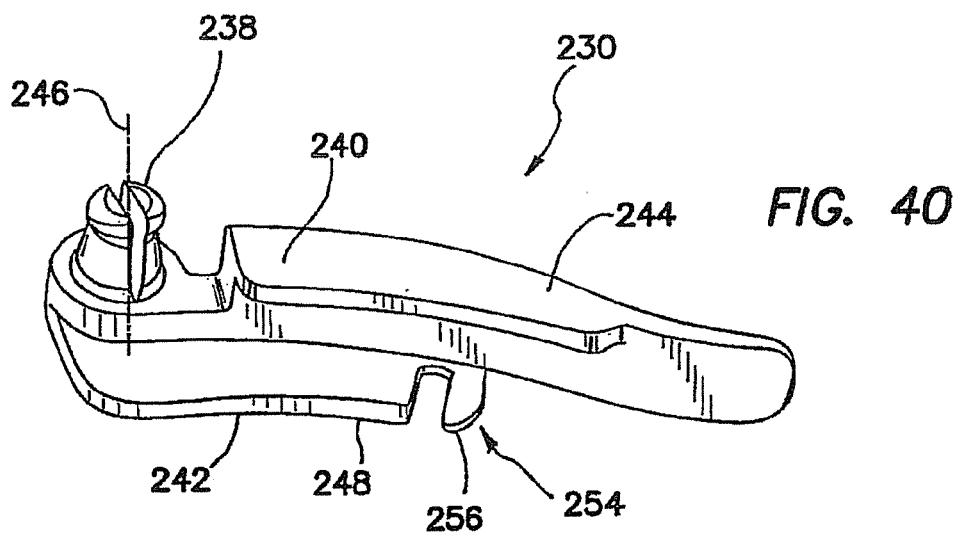
FIG. 40 is a top perspective view of the lever portion of the gel cap of FIG. 36.
Figure 41:
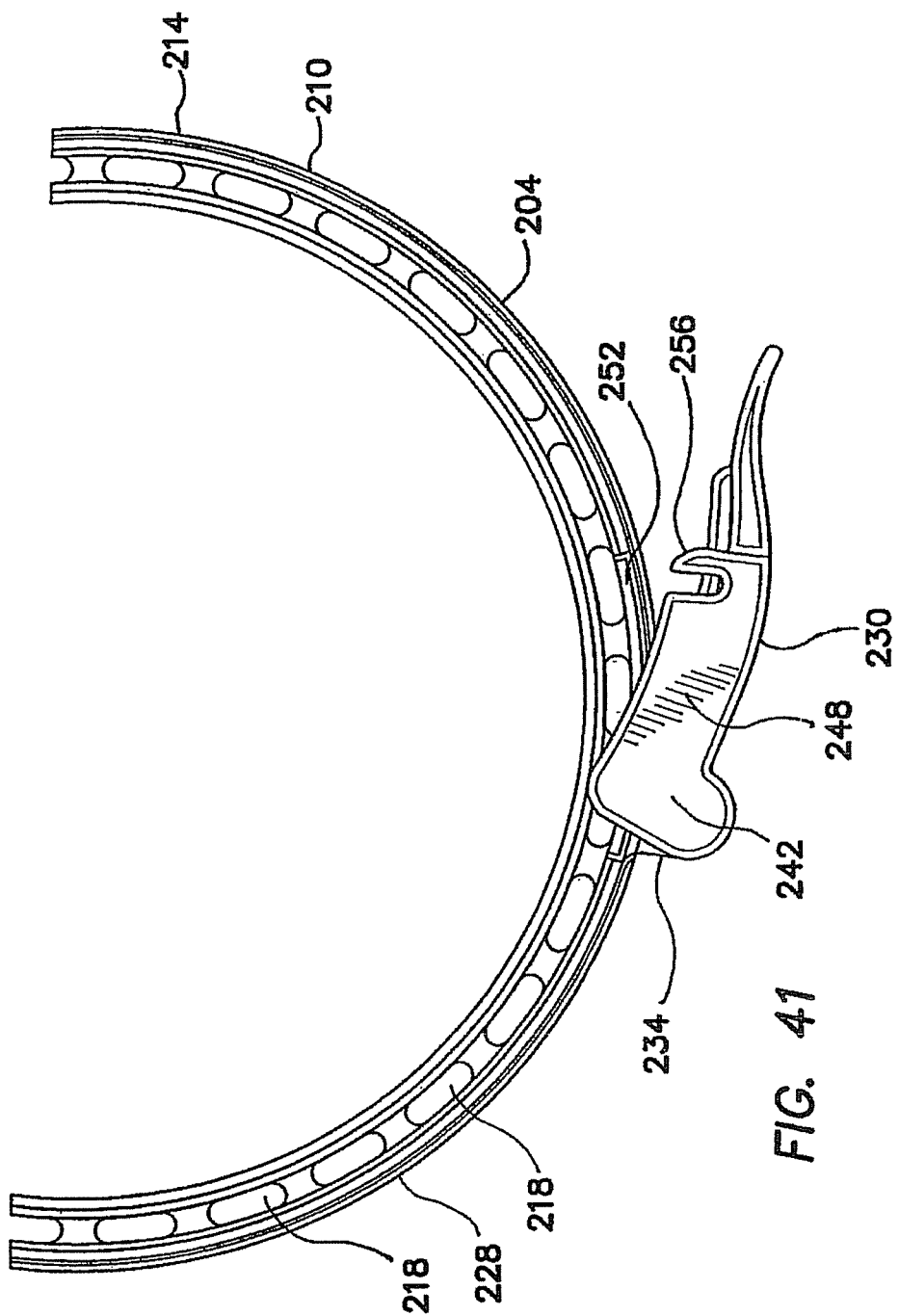
FIG. 41 is a partial bottom view of the cap ring of FIG. 36 with the lever in a first, open state.
Figure 42:
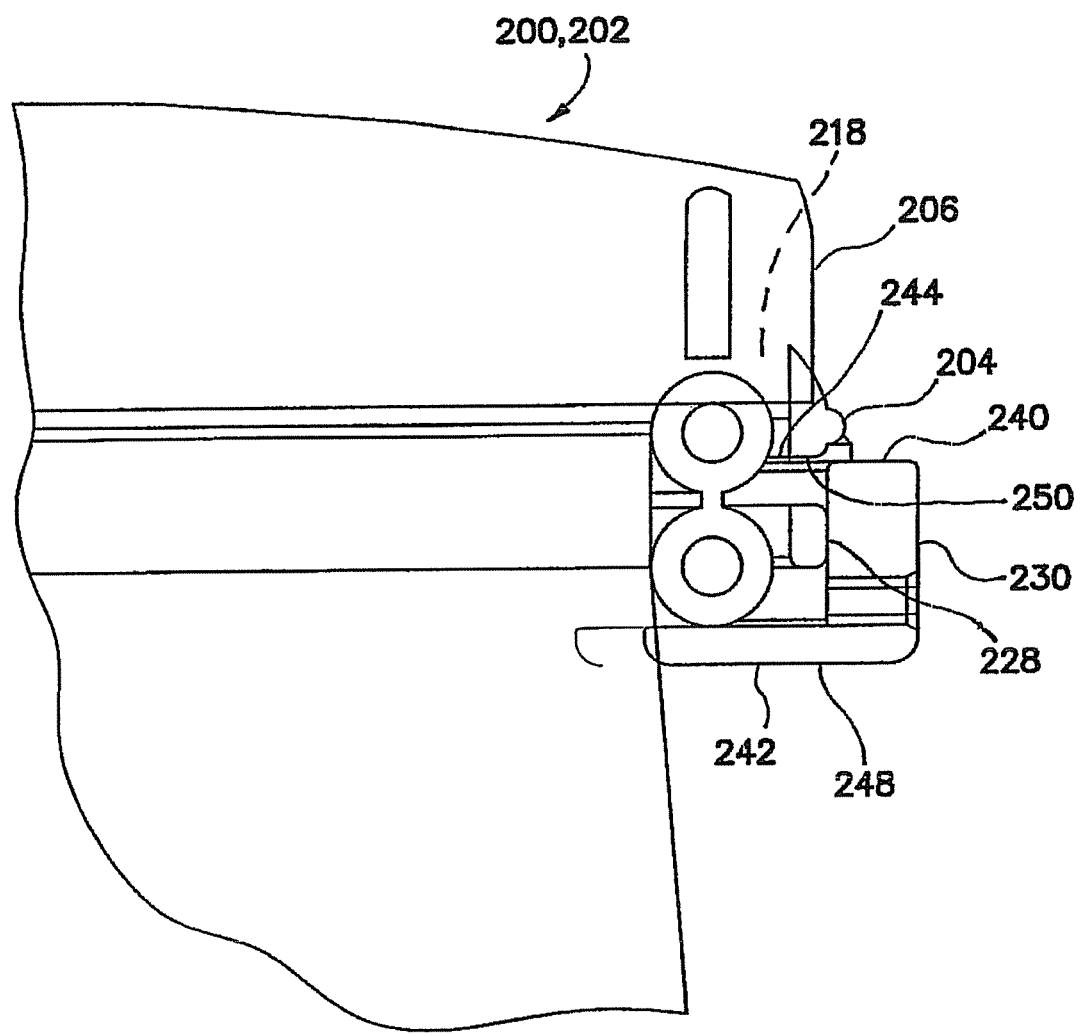
FIG. 42 is a partial section view of the gel cap of FIG. 36 coupled to the outer ring of the wound retractor with the lever in a second, closed state.

To combine the gel pad 206 with the cap ring 204, the cap ring may be placed into a mold that includes the shape of the desired gel pad and the uncured gel is added to the mold. Referring to FIG. 37, in one aspect, the cap ring 204 includes a substantially cylindrical ring 210 having a first, proximal portion 212, a second, distal portion 214 and a longitudinal axis 216 extending through the proximal and distal portions. In one aspect, the cap ring 204 may be made of a polymer, such as polycarbonate and may be fabricated by methods including injection molding. The gel pad 206 is positioned at the proximal portion 212 of the cap ring 204. The proximal portion 212 of the cap ring 204 may include a plurality of apertures 218 distributed about the circumference of the cap ring. The apertures 218 may extend through the wall of the proximal portion 212 of the cap ring 204. Sufficient gel may be added to the mold to cover and fill the apertures 218 (see FIG. 38). When adding uncured gel into the mold, the gel flows through the apertures 218 and remains in the apertures. Also, for reasons that will be described below, sufficient gel may be added to the mold to extend into the distal portion 214 of the cap ring 204. When the gel pad 206 is cured, the gel in the apertures 218 connects the gel at the outer portion 220 of the cap ring 204 to the gel at the inner portion 222 of the cap ring, thus forming a mechanical lock between the gel and the cap ring.

The distal portion 214 of the cap ring 204 is substantially cylindrical and is configured to receive the outer ring 114 of the wound retractor 100. In one aspect, the distal portion 214 of the cap ring 204 includes a lip 224 at the distal end 226 thereof (see FIG. 37). The lip 224 curves radially inwardly from the wall 228 of the distal portion 214 of the cap ring 204 and extends around a portion of the circumference of the cap ring. In one aspect, the lip 224 extends around about 30° of the circumference of the cap ring 204; however, the lip may extend longer or shorter distances around the circumference of the cap ring. The lip 224 is configured to receive the outer ring 114 such that the outer ring is positioned between the lip 224 and the gel pad 206 (see FIG. 39). More particularly, when the outer ring 114 of the wound retractor 100 is received by the distal portion 214 of the cap ring 204, the outer ring of the wound retractor embeds into the gel pad 206 at the distal portion of the cap ring and displaces the gel, thereby forming a seal between the gel pad and the outer ring and sleeve 116 of the wound retractor.

In one aspect, the distal portion 214 of the cap ring 204 also includes a swinging lever 230 (FIG. 36) that swings on a plane that is substantially perpendicular to the axis 216 of the cap ring. In one aspect, the lever 230 is positioned substantially opposite the lip 224 on the distal portion 214 of the cap ring 204. The outer surface 232 of the cap ring 204 may include a lug 234 to which the lever 230 is coupled. In one aspect, the lug 234 includes an aperture 236 extending substantially parallel to the longitudinal axis 216 of the cap ring 204 and is adapted to receive a hinge pin 238 portion of the lever 230. When coupled to the cap ring 204, the lever 230 includes a proximal end 240 and a distal end 242. The lever 230 includes a first, distal substantially flat lip 244 positioned at the distal end 242 of the lever and lying in a plane that is positioned substantially perpendicular to the axis 246 of the pin 238 on the lever. It should be noted that the axis 246 of the pin 238 on the lever 230 is substantially parallel to the longitudinal axis 216 of the cap ring 204. The lever 230 may also include a second, proximal substantially flat lip 248 positioned at the proximal end 240 of the lever and also lying in a plane that is substantially perpendicular to an axis 246 of the pin 238 on the lever such that the proximal lip of the lever is substantially parallel to the distal lip 244 of the lever. Both of the distal and proximal lips 244, 248 of the lever 230 extend from the same side of the lever.

In a first, open state (FIG. 41), the lever 230 is swung outwardly, away from the body of the cap ring 204 to provide clearance for inserting the outer ring 114 of the wound retractor 100 into the gel cap. In a second, closed state (FIG. 42), the lever 230 is swung toward the cap ring 204 such that the distal and proximal lips 244, 248 of the lever protrude radially inwardly from the body of the lever and radially inwardly through the wall 228 of the cap ring. In one aspect, the wall 228 of the distal portion 214 of the cap ring 204 includes a first aperture 250 or groove for receiving the distal lip 244 of the lever 230. Similarly, the wall 228 of the distal portion 214 of the cap ring 204 also includes a second aperture 252, such as a slot, for receiving and supporting the proximal lip 248 of the lever 230. In one aspect, the distal lip 244 on the lever 230 extends around about 60° of the circumference of the cap ring and the proximal lip 248 on the lever extends around about 45° of the circumference of the cap ring; however, the distal and proximal lips may extend longer or shorter distances around the circumference of the cap ring.

Figure 43:
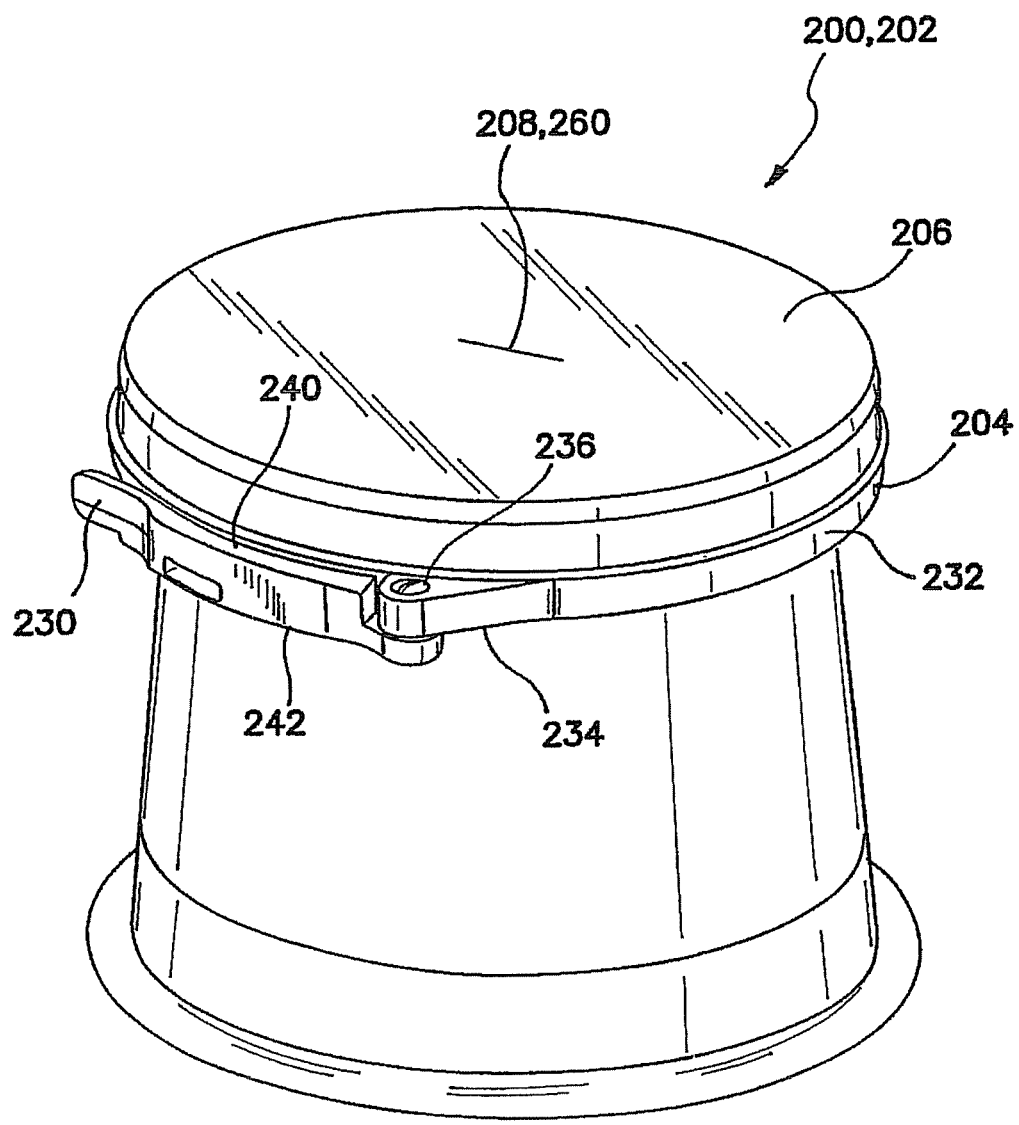
FIG. 43 is a top perspective view of the gel cap of FIG. 36 coupled to the wound retractor.
Figure 44:
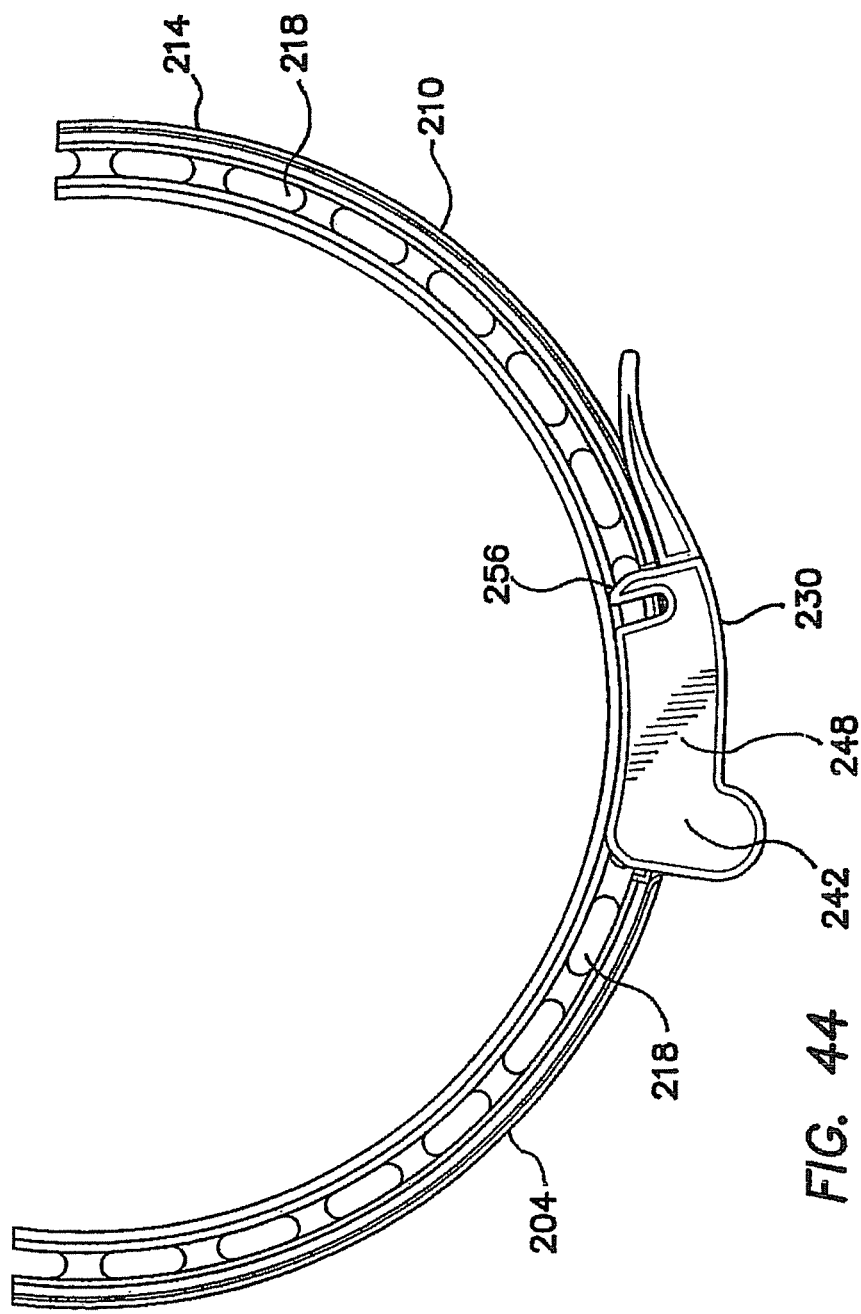
FIG. 44 is a partial bottom view of the cap ring of FIG. 36 with the lever in the second, closed state.
Figure 45:
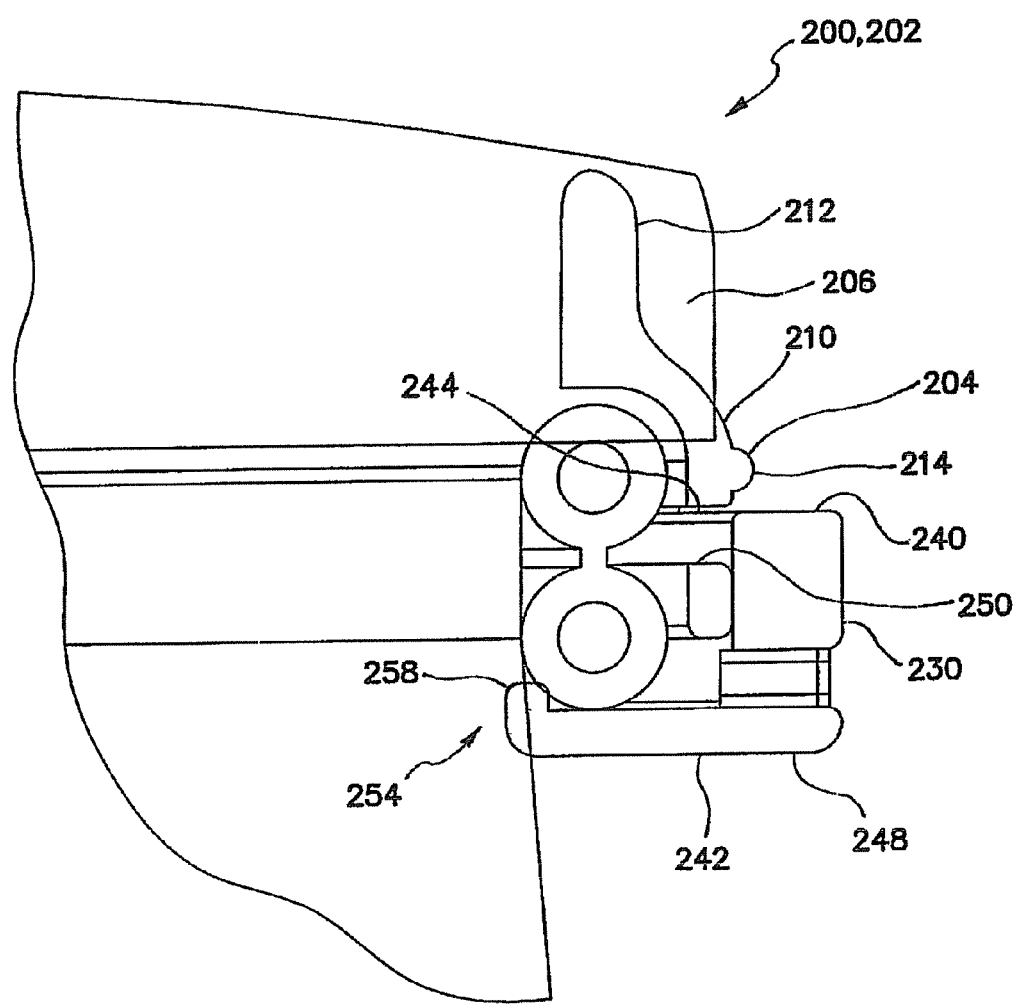
FIG. 45 is a partial section view of the gel cap of FIG. 36 coupled to the outer ring of the wound retractor with the lever in a second, closed state and the lever having a catch for engaging the outer ring of the wound retractor to hold the lever in the closed state.
Figure 46:
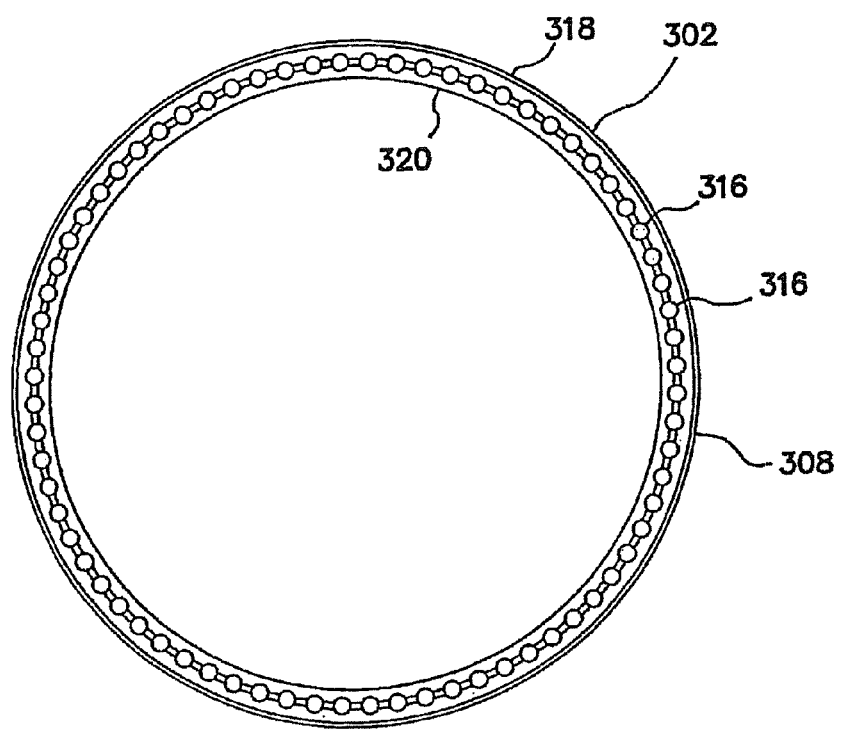
FIG. 46 is a top plan view of a cap ring portion of a gel cap of the invention configured for coupling the gel cap to the outer ring of the wound retractor.
Figure 49:
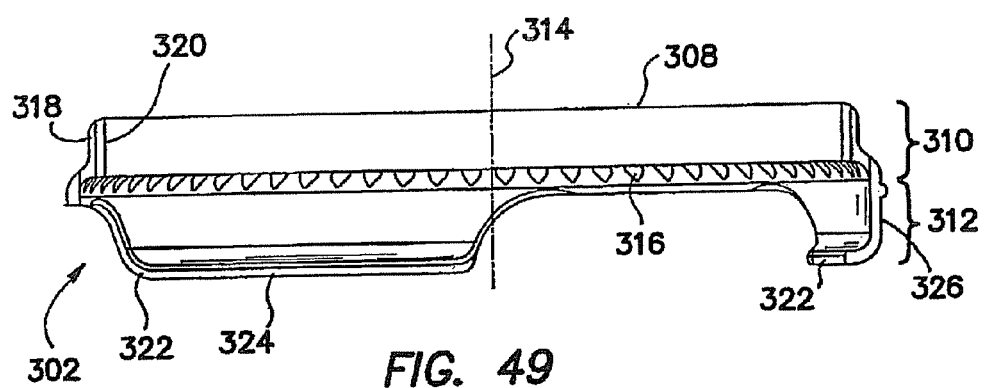
FIG. 49 is a side cross-sectional view of the cap ring of FIG. 46.
Figure 47:
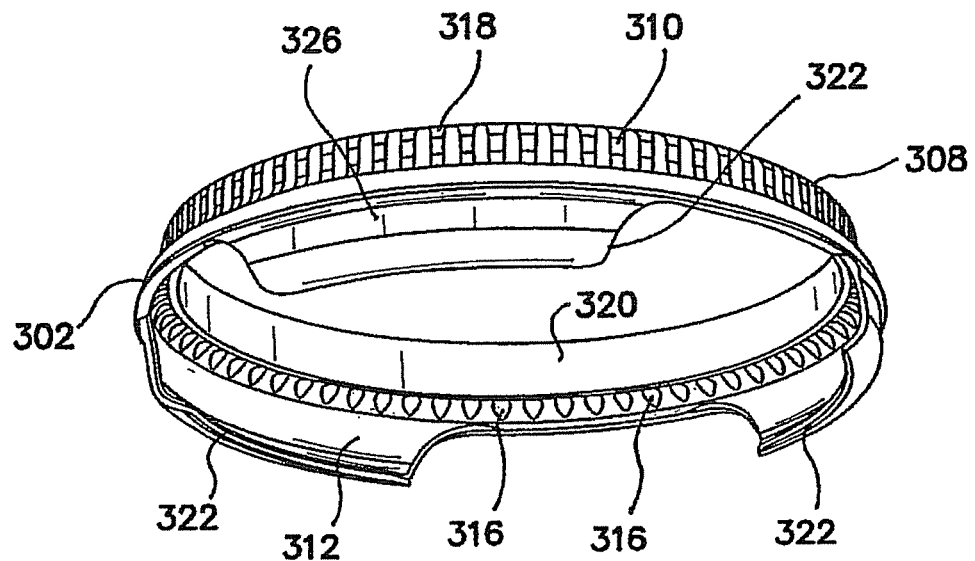
FIG. 47 is a bottom perspective view of the cap ring of FIG. 46 depicting lips for engaging the outer ring of the wound retractor.
Figure 48:
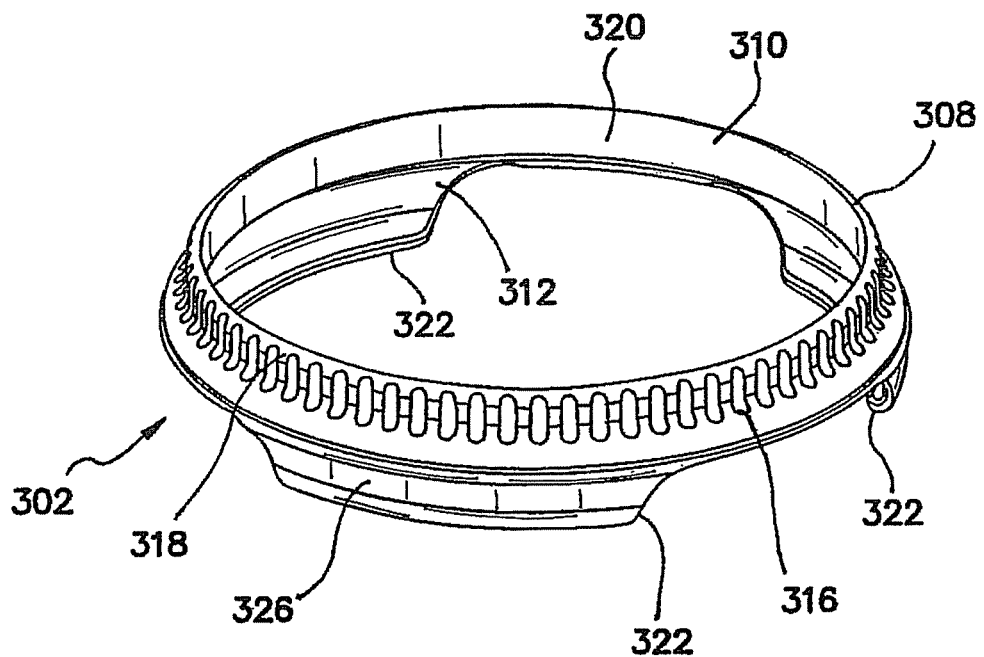
FIG. 48 is a top perspective view of the cap ring of FIG. 46.
Figure 50:
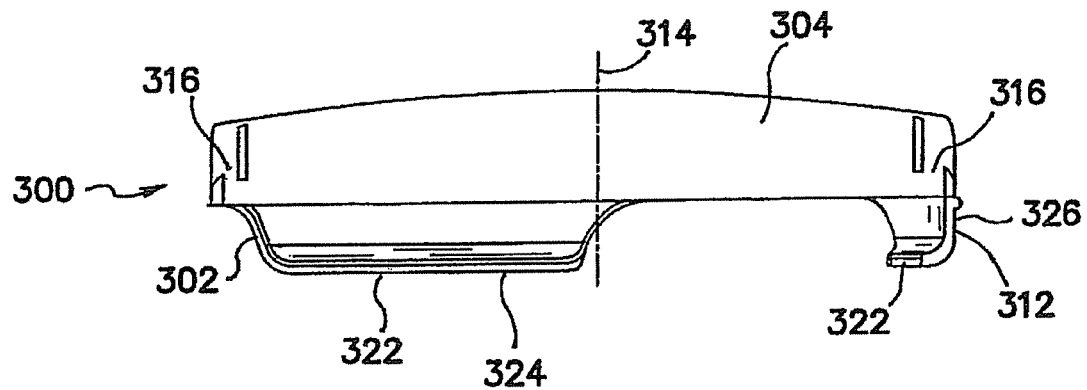
FIG. 50 is a side cross-sectional view of the gel cap incorporating the cap ring of FIG. 46.
Figure 51:
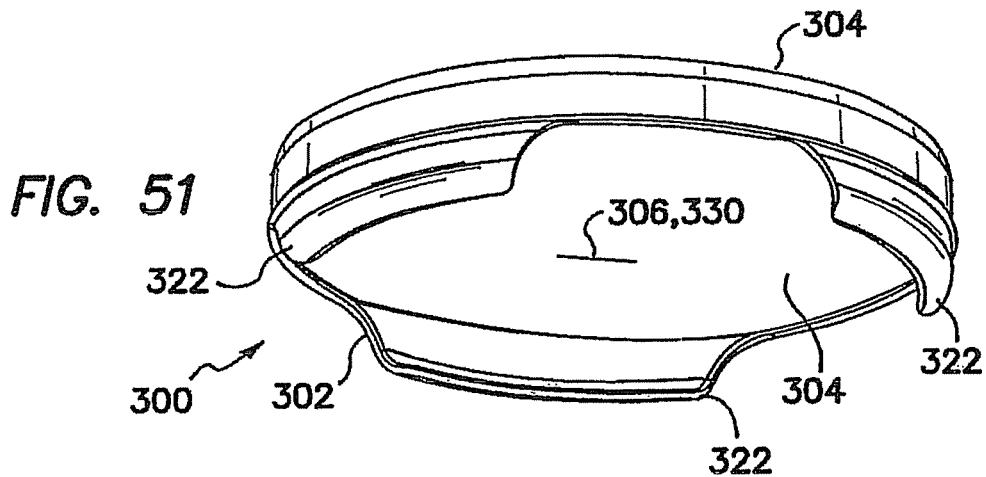
FIG. 51 is a bottom perspective view of the gel cap of FIG. 50.
Figure 52:
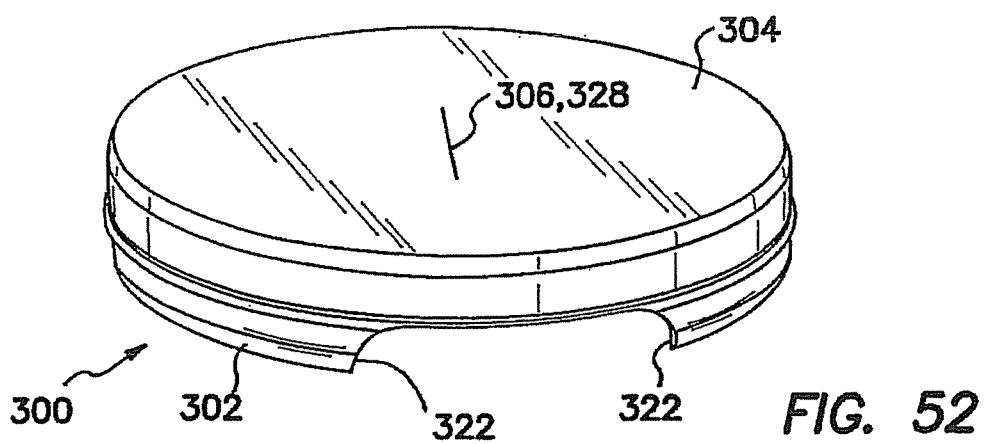
FIG. 52 is a top perspective view of the gel cap of FIG. 50.
Figure 53:
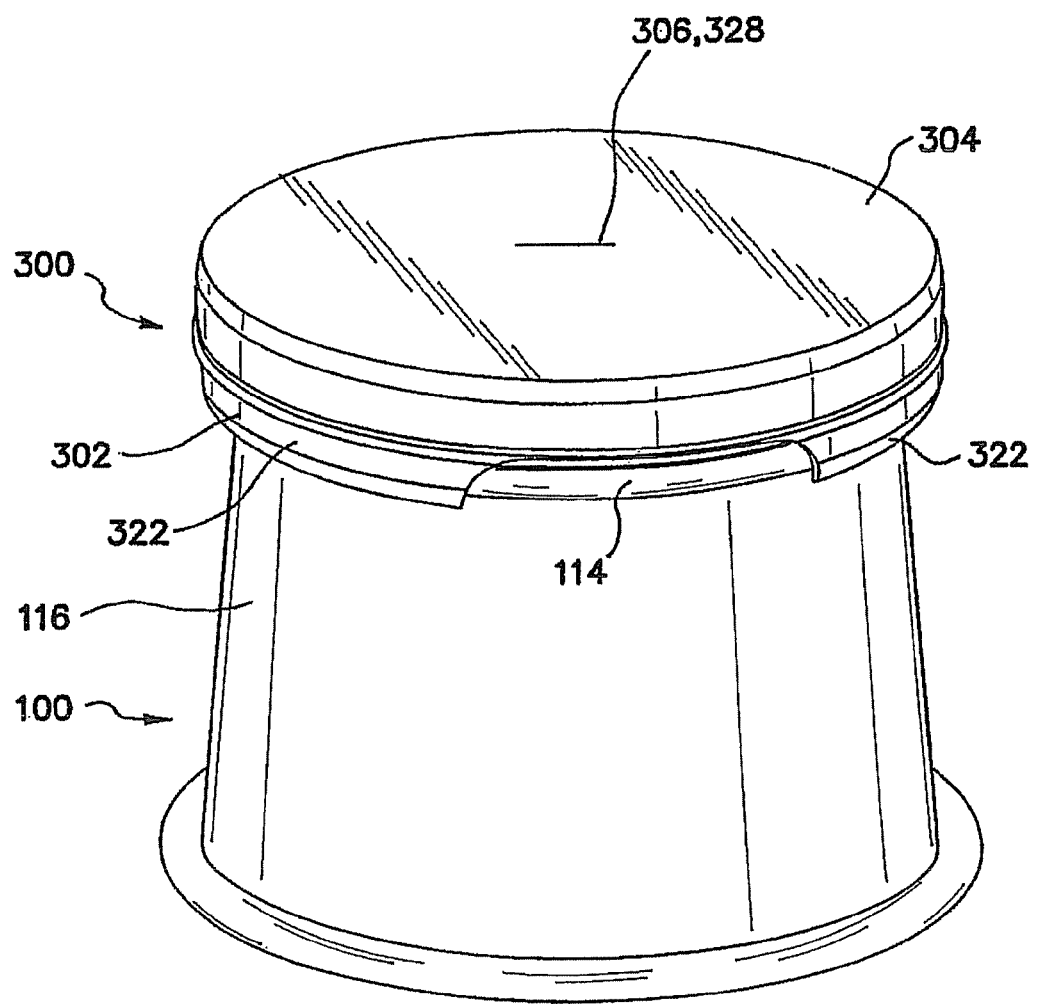
FIG. 53 is a top perspective view of the gel cap of FIG. 50 coupled to the outer ring of the wound retractor.
Figure 54:
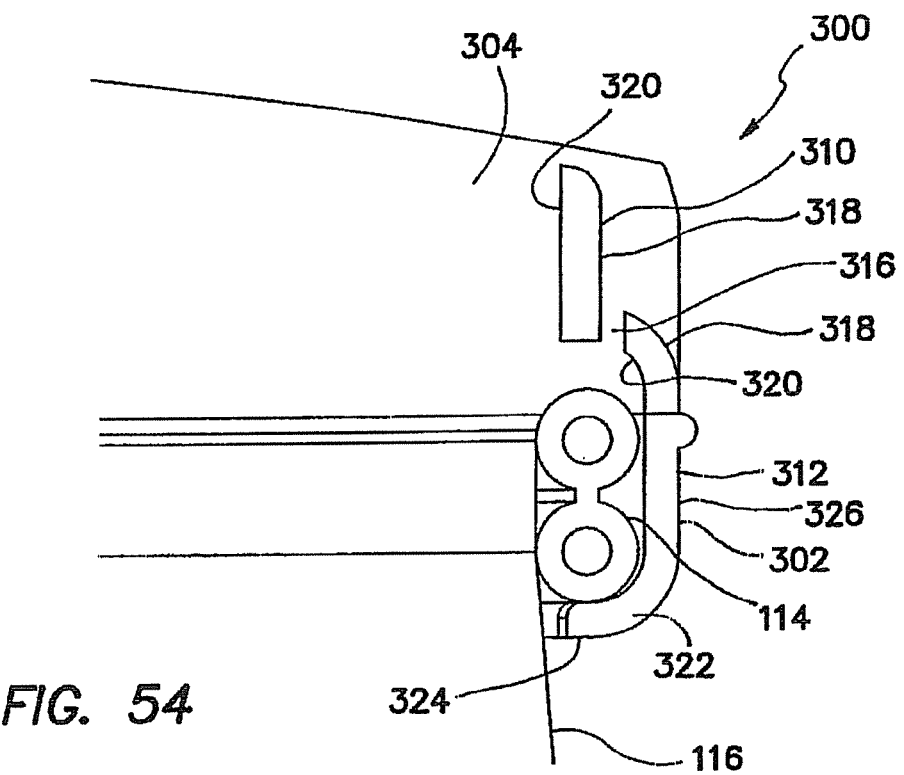
FIG. 54 is a partial section view of the gel cap of FIG. 50 coupled to the outer ring of the wound retractor.
Figure 55:
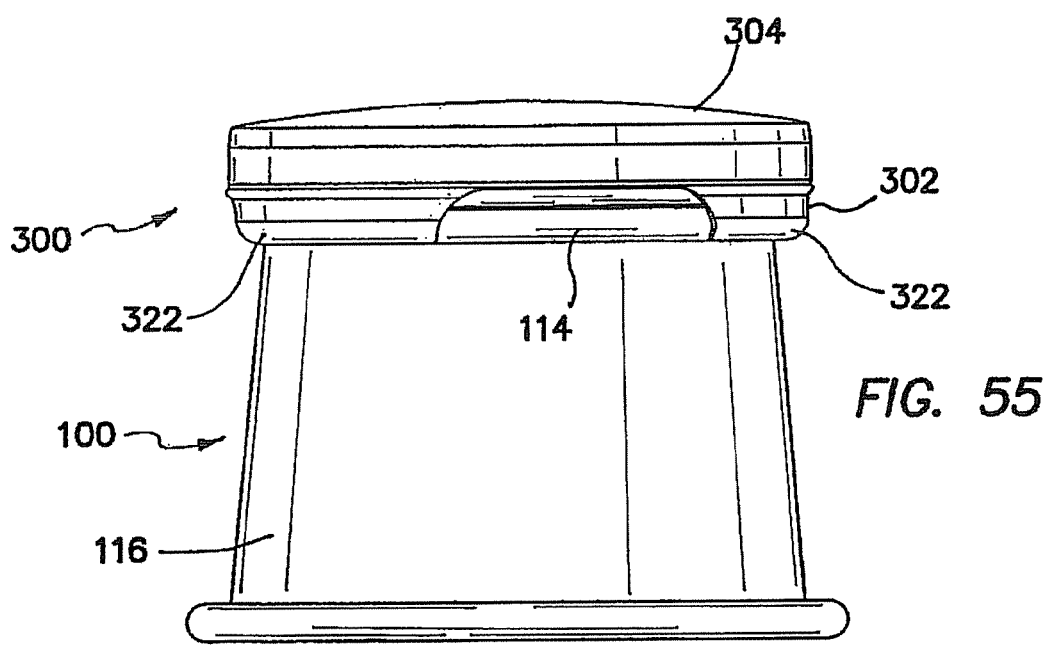
FIG. 55 is a side view of the gel cap of FIG. 50 coupled to the outer ring of the wound retractor.

In use, the wound retractor 100 is first used to retract the incision in the body wall 104 of a patient 106, as described above. With the lever 230 in the first state, the gel cap 202 is brought to the outer ring 114 of the wound retractor 100 at an angle with the lip portion 224 of the cap ring 204 toward the patient 106. The lip portion 224 of the cap ring is slid under the outer ring 114, between the outer ring and the patient 106, and then the remainder of the gel cap 202 is swung onto the outer ring. The lever 230 is then swung closed into the second state (FIG. 43). In the second state, the distal lip 244 of the lever 230 abuts the distal surface of the outer ring 114 of the wound retractor 100 and secures the gel cap 202 to the wound retractor. More particularly, with the gel cap 202 mounted onto the outer ring 114 of the wound retractor 100 and the lever 230 positioned in the second state, the lip portion 224 of the cap ring 204 and the distal lip 244 of the lever receive the outer ring of the wound retractor. The outer ring 114 of the wound retractor 100 is positioned between the lip portion 224 of the cap ring 204 and the distal lip 244 of the lever 230 at the distal end of the outer ring of the wound retractor and the gel pad 206 at the proximal end of the outer ring of the wound retractor.

The lever 230 includes locking means 254 (FIG. 40) to prevent unintended opening of the lever from the second state to the first state. In one aspect, to positively lock the lever 230 into the second state, one of the distal and proximal lips 244, 248 of the lever includes a latch 256 that engages the groove/aperture 250, 252 in the cap ring through which the lip protrudes (see FIG. 44). In another aspect, the distal lip 244 of the lever 230 includes a catch 258 (FIG. 45) protruding proximally to engage the outer ring 114 of the wound retractor 100 at a position on the inner circumference of the outer ring.

With the gel cap 202 mounted onto the outer ring 114 of the wound retractor 100 and the lever 230 positioned in the second state, the proximal lip 248 on the lever positioned in the aperture 252 in the cap ring 204 provides support for the lever to counteract cantilever forces induced by the displaced gel of the gel pad 206. Support of the proximal lip 248 also helps the distal lip 244 maintain the position of the outer ring 114 of the wound retractor 100 against the gel pad 206.

In another aspect, the gel cap 202 may include more than one lever 230 with the levers substantially equally spaced between each other and the lip 224 on the cap ring 204. In a further aspect, the lip 224 on the cap ring 204 may be omitted and at least two levers 230 used to secure the gel cap 202 to the wound retractor 100.

Referring to FIGS. 46-55, a gel cap 300 includes a cap ring 302 that couples to the outer ring 114 of the wound retractor 100 and a gel pad 304 coupled to the cap ring. The gel pad 304 is made of a gel material and includes an access portion 306 or passage through the gel for providing a passage from external the body to the body cavity 110. In one aspect, the access portion 306 may include a plurality of intersecting dead-end slits 328, 330. The access portion 306 forms an instrument seal in the presence of an instrument, such as the arm of a surgeon, inserted therethrough and a zero seal in the absence of an instrument inserted therethrough.

To combine the gel pad 304 with the cap ring 302, the cap ring may be placed into a mold that includes the shape of the desired gel pad and the uncured gel is added to the mold. In one aspect, the cap ring 302 includes a substantially cylindrical ring 308 having a first, proximal portion 310, a second, distal portion 312 and a longitudinal axis 314 extending through the proximal and distal portions. In one aspect, the cap ring 302 may be made of a polymer, such as polycarbonate and may be fabricated by methods including injection molding. The gel pad 304 is positioned at the proximal portion 310 of the cap ring 302. The proximal portion 310 of the cap ring 302 may include a plurality of apertures 316 distributed about the circumference of the cap ring. The apertures 316 may extend through the wall of the proximal portion 310 of the cap ring 302. Sufficient gel may be added to the mold to cover and fill the apertures 316. When adding uncured gel into the mold, the gel flows through the apertures 316 and remains in the apertures. Also, for reasons that will be described below, sufficient gel may be added to the mold to extend into the distal portion 312 of the cap ring 302. When the gel pad 304 is cured, the gel in the apertures 316 connects the gel at the outer portion 318 of the cap ring 302 to the gel at the inner portion 320 of the cap ring, thus forming a mechanical lock between the gel and the cap ring.

The distal portion 312 of the cap ring 302 is substantially cylindrical and is configured to receive the outer ring 114 of the wound retractor 100. In one aspect, the distal portion 312 of the cap ring 302 includes a plurality of lips 322 at the distal end 324 thereof. The lips 322 curve radially inwardly from the wall 326 of the distal portion 312 of the cap ring 302 and extend around a portion of the circumference of the cap ring. In one aspect, there are three lips 322 that are substantially equally spaced about the circumference of the distal portion 312 of the cap ring 302. Each of the three lips 322 may extend about 60° around of the circumference of the cap ring 302, however, the lips may extend longer or shorter distances around the circumference of the cap ring. Also, there may be more than three lips 322 with each lip extending a shorter distance around the circumference of the cap ring 302 and the more than three lips being substantially equally spaced about the circumference of the distal portion of the cap ring. In another aspect, there may be two lips 322 that are substantially diametrically opposed about the circumference of the distal portion of the cap ring with each of the lips extending a sufficient distance around the circumference of the cap ring 302 to facilitate adequate coupling of the gel cap 300 to the outer ring 114 of the wound retractor 100. The lips 322 are configured to receive the outer ring 114 of the wound retractor 100 such that the outer ring is positioned between the lips 322 and the gel pad 304. More particularly, when the outer ring 114 of the wound retractor 100 is received by the distal portion 312 of the cap ring 302, the outer ring of the wound retractor embeds into the gel pad 304 at the distal portion 312 of the cap ring 302 and displaces the gel, thereby forming a seal between the gel pad and the outer ring and sleeve 116 of the wound retractor.

In use, the wound retractor 100 is first used to retract the incision 102 in the body wall 104 of a patient 106, as described above. The gel cap 300 is brought to the outer ring 114 of the wound retractor 100 at an angle, with one of the lip portions 322 of the cap ring 302 toward the patient 106. The lip portion 322 of the cap ring that is toward the patient 106 is slid under the outer ring 114, between the outer ring and the patient, and then the remainder of the gel cap 300 is swung onto the outer ring with the remaining lip portions snapping into place under the distal-most circular tube. In an alternative aspect, the gel cap 300 may be brought to the outer ring 114 substantially parallel to the outer ring and the lip portions 322 snapped into place under the outer ring at the same time.

An advantage associated with the modified surgical access device is it enables a surgeon to quickly retract and protectively line an abdominal wall incision while being able to easily accommodate variations in abdominal wall thickness between patients. In addition, the device effectively seals around the interior and exterior of the incision, and allows a sealing cap to be coupled to the device to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of the embodiments.

What is claimed is:

1. A wound retractor adapted to retract a surgical incision in a body wall, comprising:
   a first, inner ring adapted to be inserted into the incision and to be juxtaposed with an inner surface of the body wall;
   a second, outer ring adapted for juxtaposition with an outer surface of the body wall, the outer ring comprising three substantially circular tubes, substantially coaxially aligned and coupled together such that the third tube is disposed between the first and second tubes, the first tube having a first lumen and the second tube having a second lumen;
   a first rigid, noncompliant tubular hoop having a split therein, the first tubular hoop being positioned in the first lumen of the first circular tube of the outer ring, a second rigid, noncompliant tubular hoop having a split therein, the second tubular hoop being positioned in the second lumen of the second circular tube of the outer ring;
   a first core positioned in the lumen of the first tubular hoop;
   a second core positioned in the lumen of the second tubular hoop; and
   a distensible sleeve, the sleeve including a first, distal end and a second, proximal end, the first, distal end of the sleeve being coupled to the inner ring of the wound retractor and the second proximal end of the sleeve being coupled to the outer ring of the wound retractor.

2. The wound retractor of claim 1, wherein at least one of the first and second cores comprises a substantially rigid, noncompliant wire.

3. The wound retractor of claim 1, wherein the third circular tube includes a third lumen.

4. The wound retractor of claim 3, wherein the hollow third circular tube provides additional resilience that facilitates the passage of the first and second circular tubes through each other.

5. The wound retractor of claim 1, wherein the diameter of the third circular tube is less than the diameter of either the first circular tube or the second circular tube.

6. The wound protector of claim 1, wherein the first and second circular tubes are adapted to provide a detent or snap-over as the first and second circular tubes are sequentially rolled over the third circular tube.

7. The wound retractor of claim 1, wherein the third circular tube is solid.

8. The wound retractor of claim 7, wherein the solid third circular tube functions as a resilient axle about which each of the first and second circular tube may rotate.

9. The wound retractor of claim 1, wherein at least one of the first and second tubular hoops comprises a metallic material and at least one of the first and second cores comprises a metallic material.

10. The wound retractor of claim 1, wherein at least one of the first and second tubular hoops comprises a metallic material and at least one of the first and second cores comprises a composite material.

11. The wound retractor of claim 1, wherein at least one of the first and second tubular hoops comprises a composite material and at least one of the first and second cores comprises a metallic material.

12. The wound retractor of claim 1, wherein at least one of the first and second tubular hoops comprises a composite material and at least one of the first and second cores comprises a composite material.

13. A wound retractor adapted to retract a surgical incision in a body wall, comprising:
 a first, inner ring adapted to be inserted into the incision and to be juxtaposed with an inner surface of the body wall;
 a second, outer ring adapted for juxtaposition with an outer surface of the body wall, the outer ring comprising three substantially circular tubes, substantially coaxially aligned and coupled together such that the third tube is disposed between the first and second tubes, the third tube having a lumen;
 a rigid, noncompliant tubular hoop having a split therein, the tubular hoop being positioned in the lumen of the third circular tube of the outer ring; and
 a distensible sleeve, the sleeve including a first, distal end and a second, proximal end, the first, distal end of the sleeve being coupled to the inner ring of the wound retractor and the second proximal end of the sleeve being coupled to the outer ring of the wound retractor.

14. The wound retractor of claim 13, wherein the at least one of the first and second circular tubes includes a lumen.

15. The wound retractor of claim 13, wherein the first and second circular tubes are solid.

16. The wound retractor of claim 13, further comprising a core disposed within the rigid tubular hoop of the third circular tube.

17. The wound protector of claim 13, wherein the first and second circular tubes are adapted to provide a detent or snap-over as the first and second circular tubes are sequentially rolled over the third circular tube.

18. The wound retractor of claim 13, wherein the rigid, noncompliant hoop of the third circular tube functions as an axle about which each of the first and second circular tube may rotate.

19. The wound retractor of claim 13, wherein the diameter of the third circular tube is less than the diameter of either the first circular tube or the second circular tube.

20. The wound retractor of claim 13, wherein the three circular tubes are of substantially equal diameter.

* * * * *